(12) United States Patent
Maskara et al.

(10) Patent No.: US 8,954,138 B2
(45) Date of Patent: Feb. 10, 2015

(54) USING DEVICE BASED ELECTROGRAMS TO IDENTIFY BUNDLE BRANCH BLOCK MORPHOLOGY

(71) Applicant: Cardiac Pacemakers, Inc., St. Paul, MN (US)

(72) Inventors: Barun Maskara, Blaine, MN (US); Shibaji Shome, Arden Hills, MN (US); Pramodsingh Hirasingh Thakur, White Bear Lake, MN (US); Abhilash Patangay, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 42 days.

(21) Appl. No.: 13/677,962

(22) Filed: Nov. 15, 2012

(65) Prior Publication Data

US 2013/0123653 A1 May 16, 2013

Related U.S. Application Data

(60) Provisional application No. 61/560,445, filed on Nov. 16, 2011.

(51) Int. Cl.
*A61B 5/0472* (2006.01)
*A61B 5/0456* (2006.01)
*A61B 5/00* (2006.01)
*A61N 1/362* (2006.01)

(52) U.S. Cl.
CPC .............. *A61B 5/0472* (2013.01); *A61B 5/0456* (2013.01); *A61B 5/746* (2013.01); *A61B 5/686* (2013.01); *A61N 1/3627* (2013.01)

USPC .............................................. 600/516; 607/25

(58) Field of Classification Search
USPC .................................. 607/9, 25; 600/515–516
See application file for complete search history.

(56) References Cited

U.S. PATENT DOCUMENTS

| 5,527,347 | A | 6/1996 | Shelton et al. |
| 5,683,426 | A | 11/1997 | Greenhut et al. |
| 6,129,744 | A | 10/2000 | Boute |

(Continued)

FOREIGN PATENT DOCUMENTS

WO WO-03037427 A1 5/2003

OTHER PUBLICATIONS

"Left bundle branch block", Wikipedia http://en.wikipedia.org/wiki/Left_bundle_branch_block, 3 pgs.

(Continued)

*Primary Examiner* — Rex R Holmes
(74) *Attorney, Agent, or Firm* — Schwegman Lundberg & Woessner, P.A.

(57) ABSTRACT

A patient QRS duration can be received or determined, such as using one or more patient physiological sensors. A portion of the QRS duration can be determined, such as a right or left ventricular activation time. In an example, the right ventricular activation time can be determined by identifying an onset of a QRS complex and an R-wave peak in the QRS complex. In an example, when the QRS duration exceeds a threshold duration, and the RV activation time does not exceed a second threshold duration, an indication of a cardiac conduction dysfunction can be provided, such as for discriminating between left bundle branch block and right bundle branch block.

19 Claims, 14 Drawing Sheets

(56) References Cited

U.S. PATENT DOCUMENTS

| | | |
|---|---|---|
| 6,370,427 B1 | 4/2002 | Alt et al. |
| 6,622,040 B2 | 9/2003 | Ding et al. |
| 6,766,189 B2 | 7/2004 | Yu et al. |
| 6,804,555 B2 | 10/2004 | Warkentin |
| 6,999,815 B2 | 2/2006 | Ding et al. |
| 7,181,285 B2 | 2/2007 | Lindh et al. |
| 7,283,864 B2 | 10/2007 | Thomas et al. |
| 7,313,433 B2 | 12/2007 | Yu et al. |
| 7,395,216 B2 | 7/2008 | Rosenfeld et al. |
| 7,546,162 B2 | 6/2009 | Ding et al. |
| 7,912,544 B1 | 3/2011 | Min et al. |
| 7,930,026 B2 | 4/2011 | Boute et al. |
| 2002/0077559 A1 | 6/2002 | Ding et al. |
| 2002/0087055 A1 | 7/2002 | Rowlandson |
| 2003/0004548 A1 | 1/2003 | Warkentin |
| 2003/0014084 A1 | 1/2003 | VanHout et al. |
| 2003/0204215 A1 | 10/2003 | Gunderson et al. |
| 2004/0059237 A1 | 3/2004 | Narayan et al. |
| 2007/0250125 A1 | 10/2007 | Lindh et al. |
| 2008/0071183 A1 | 3/2008 | Thomas et al. |
| 2008/0097542 A1 | 4/2008 | Yu et al. |
| 2008/0306568 A1 | 12/2008 | Ding et al. |
| 2009/0093861 A1 | 4/2009 | Ortega et al. |
| 2009/0270937 A1 | 10/2009 | Yonce et al. |
| 2010/0069987 A1 | 3/2010 | Min et al. |
| 2011/0125041 A1 | 5/2011 | Fischell et al. |
| 2011/0137368 A1* | 6/2011 | Lindh et al. .................. 607/25 |
| 2012/0310101 A1 | 12/2012 | Patangay et al. |

OTHER PUBLICATIONS

"The Multicenter Automatic Defibrillator Implantation Trial-Cardiac Resynchronization Therapy (MADIT-CRT)", http://www.bostonscientific.com/cardiac-rhythm-resources/clinical/madit-crt-trial.html, 3 pgs.

Zareba, Wojciech, et al., "Effectiveness of Cardiac Resynchronization Therapy by QRS Morphology in the Multicenter Automatic Defibrillator Implantation Trial Cardiac Resynchronization Therapy (MADIT-CRT)", Circulation Journal of the American Heart Association, (Feb. 28, 2011), 13 pgs.

"International Application Serial No. PCT/US2012/065273, International Preliminary Report on Patentability mailed May 30, 2014", 9 pgs.

"International Application Serial No. PCT/US2012/065273, International Search Report mailed Feb. 19, 2013", 3 pgs.

"International Application Serial No. PCT/US2012/065273, Written Opinion mailed Feb. 19, 2013", 7 pgs.

"U.S. Appl. No. 61/491,459, filed May 31, 2011", 45 pgs.

* cited by examiner

USING DEVICE BASED ELECTROGRAMS TO IDENTIFY BUNDLE BRANCH BLOCK MORPHOLOGY

CLAIM OF PRIORITY

This application claims the benefit of priority under 35 U.S.C. §119(e) of Maskara et al., U.S. Provisional Patent Application Ser. No. 61/560,445, entitled "USING DEVICE BASED ELECTROGRAMS TO IDENTIFY BUNDLE BRANCH BLOCK MORPHOLOGY", filed on Nov. 16, 2011, which is herein incorporated by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter-defibrillators (ICDs), cardiac resynchronization therapy devices (CRTs), or devices that include a combination of these capabilities or others. The devices can be used to treat patients or subjects using electrical or other therapies, or to aid a physician or caregiver in patient diagnosis through monitoring of a patient condition. The devices can include one or more electrodes in communication with one or more sense amplifiers to monitor electrical heart activity within a patient, and can include one or more sensors to monitor one or more other internal patient parameters. Other examples of IMDs include implantable diagnostic devices, implantable drug delivery systems, or implantable devices with neural stimulation capability.

In addition to IMDs, medical devices also include other ambulatory medical devices, such as wearable medical devices (WMDs), such as wearable cardioverter defibrillators (WCDs). WCDs can include monitors that can include surface electrodes. The surface electrodes can be arranged to provide one or both of monitoring surface electrocardiograms (ECGs) or delivering cardioversion or defibrillation shock therapy.

Some medical devices can include one or more sensors to monitor a physiologic status of a patient. For example, a device can be configured to measure a cardiac depolarization of the patient, a thoracic impedance, or a patient posture, among other things. Such measurements can provide useful information concerning the health of the patient, such as can be used to indicate a therapy.

Methods and devices to assess cardiac function using information about ventricular activity and a QRS interval can be found in Boute et al., U.S. Pat. No. 7,930,026, entitled "MONITORING QRS COMPLEX TO IDENTIFY LEFT VENTRICULAR DYSFUNCTION."

OVERVIEW

This document relates generally to systems, devices, and methods that can be used to monitor cardiac function or to provide therapy to a patient. The present inventors have recognized, among other things, that a problem to be solved can include identifying ventricular cardiac dysfunction. In an example, ventricular cardiac dysfunction can include left or right bundle branch block, or intraventricular conduction delay. In an example, the present subject matter can provide a solution to this problem, such as by using one or more electrogram signals to provide an indication of ventricular dysfunction or to help distinguish between different types of ventricular dysfunction.

In an example, a patient QRS duration can be received or determined from a patient electrogram (e.g., an electrocardiogram), such as can be obtained using one or more implanted or external patient physiological sensors. The QRS complex morphology can represent the health of the myocardium, including the left and right sides. In an example, the QRS duration can be extended, such as indicating a delayed activation of a portion of the myocardium (e.g., one of the left or right side) relative to a different portion of the myocardium (e.g., the other one of the left or right side).

In an example, a portion of the QRS duration can be determined, such as a right or left ventricular activation time. In an example, the right ventricular activation time can be determined by identifying an onset of a QRS complex and a corresponding R-wave peak in the QRS complex, such as using an electrogram obtained using an electrode disposed in or near the right ventricle. In an example, when the QRS duration exceeds a threshold duration, and the RV activation time does not exceed a second threshold duration, an indication of a cardiac conduction dysfunction can be provided.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
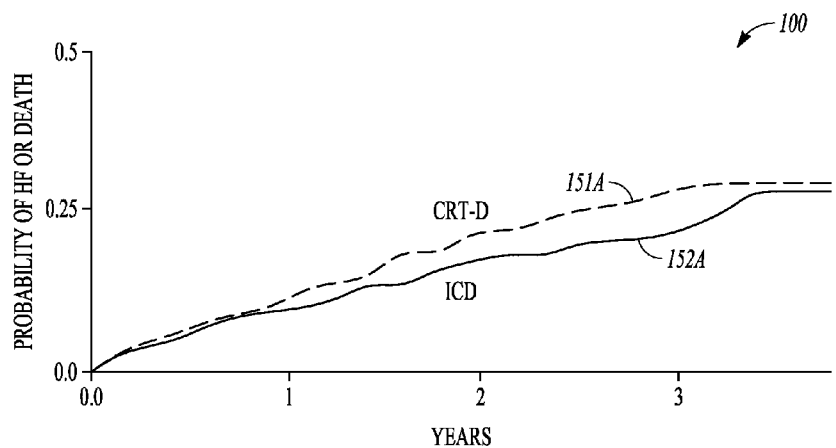
FIGS. 1A and 1B illustrate generally a relationship between a patient success rate and various cardiac therapies.
Figure 1B:
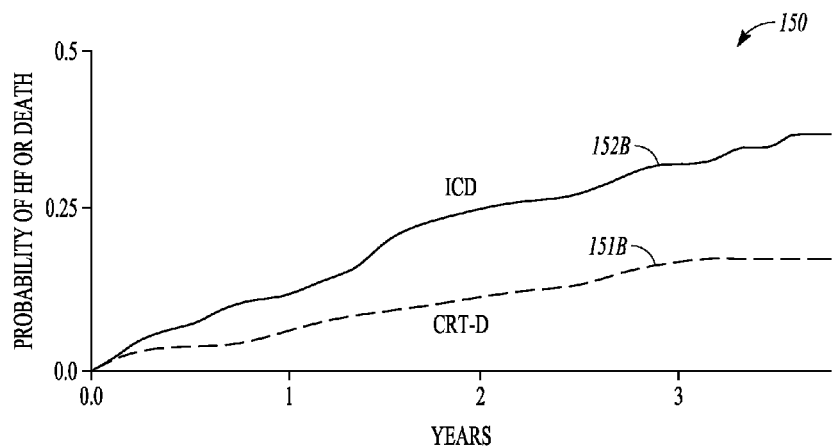

FIGS. 1A and 1B illustrate generally a relationship between a patient success rate and various cardiac therapies.

Some patients experience a cardiac conduction dysfunction, such as a right bundle branch block (RBBB), left bundle branch block (LBBB), or intraventricular conduction delay (IVCD). Such dysfunction can be caused by an underlying heart disease or myocardial infarction, among other causes.

Bundle branch block, for example, can affect one or both sides of the myocardium, and can be indicated by a delay or obstruction of the natural electrical impulses that can cause a healthy heart to contract. IVCD can similarly be associated with an electrical conduction delay. Some conditions that can lead to bundle branch block or IVCD can include one or more of myocardial infarction, or cardiomyopathy, among others, such as without a specific indication of a left or right bundle branch block.

Some patients with bundle branch block can be asymptomatic, while other patients can require treatment, such as electrostimulation therapy provided using a cardiac pacemaker. FIG. 1A illustrates generally an example 100 of an average patient success rate over time for patients who do not exhibit a bundle branch block (e.g., a left bundle branch block), such as in first and second patient populations. In an example, the first patient population, such represented using a first trendline 151a, can include patients who have available cardiac resynchronization therapy and defibrillation (CRT-D) treatments, such as using an implantable CRT-D device. In an example, the second patient population, such as represented using a second trendline 152a, can include patients who have available only implantable cardiac defibrillation (ICD) treatments. In the example of FIG. 1A, a non-left bundle branch block (non-LBBB) patient with a CRT-D device can be approximately equally likely to experience heart failure or death as a non-LBBB patient with an ICD device.

FIG. 1B illustrates generally an example 150 of an average patient success rate over time for patients who exhibit a bundle branch block (e.g., a left bundle branch block). In the example of FIG. 1B, a probability of patient heart failure or death can be compared for first and second populations, such as a first patient population that has CRT-D therapies available (represented using a third trendline 151b), and a second patient population that has ICD therapies available (represented using a fourth trendline 152b).

In the example of FIG. 1B, a left bundle branch block (LBBB) patient with a CRT-D device can be substantially less likely to experience heart failure or death than a LBBB patient with an ICD device only. That is, a LBBB patient who has a device that can provide both cardiac resynchronization therapy and defibrillation can be more likely to avoid heart failure and death than a patient who has a device that provides only cardioversion and defibrillation therapies. Patients can therefore benefit from an identification of bundle branch block cardiac morphologies. For example, where a LBBB morphology is identified in a patient, the patient can be a candidate for receiving a cardiac resynchronization device. In an example, an ICD device can be used to monitor one or more patient cardiac signals, and can be used to provide an indication that the patient is a candidate for cardiac resynchronization therapy, such as when a particular BBB morphology is indicated.

Figure 2:
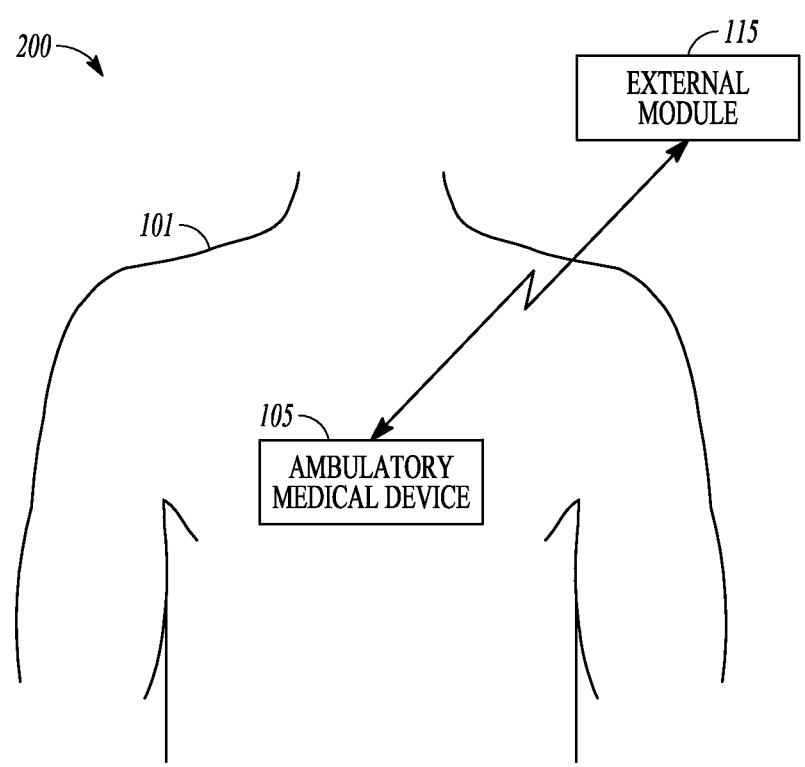
FIG. 2 illustrates generally an example of a system that can include an ambulatory medical device and an external module.

FIG. 2 illustrates generally an example of a system 200 that can include an implantable medical device (IMD) 105 or other ambulatory medical device, such as can be used to provide an indication of, or provide therapy for, a bundle branch block. In an example, the IMD 105 can include a cardiac rhythm management device, or pacemaker, such as can be configured to deliver a cardiac resynchronization therapy such as to a diseased heart. In an example, the IMD 105 can include a cardioverter-defibrillator, among other implantable medical devices. In an example, the IMD 105 can be disposed in or into a subject body 101, and the IMD 105 can be communicatively coupled to an external module 115. In an example, the IMD 105 can include an antenna configured to provide radio-frequency or other wireless communication between the IMD 105 and the external module 115, or other external device.

In an example, the IMD 105 can include one or more of a cardiac stimulating circuit, a cardiac signal sensing circuit, or a processor circuit, such as described below in the discussion of FIG. 4. A functional portion of one or more of the cardiac stimulating circuit, cardiac signal sensing circuit, or the processor circuit can be located in the IMD 105, and another portion elsewhere (e.g., in an external programmer or analyzer circuit, such as in the external module 115).

In an example, the external module 115 can include a local medical device programmer or other local external module, such as within wireless communication range of the IMD 105 antenna. In an example, the external module 115 can include a remote medical device programmer or one or more other remote external modules (e.g., outside of wireless communication range of the IMD 105 antenna, but coupled to the IMD 105 using a local external device, such as a repeater or network access point). The external module 115 can include a processor circuit that can be configured to process information that can be sent to or received from the IMD 105. The information can include medical device programming information, subject data, device data, or other instructions, indications, alerts, or other information. In an example, the external module 115 can be configured to display information (e.g., received information) to a user, such as a patient or a clinician, such as using a local patient interface. Further, the local programmer or the remote programmer can be configured to communicate the sent or received information to a user or physician, such as by sending an alert or indication via email of the status of the subject 101 or the system 200 components. In an example, the external module 115 can adjust a therapy control signal, such as can be used by the processor circuit of the IMD 105 to control a patient therapy, such as a drug or electrostimulation therapy.

Figure 3:
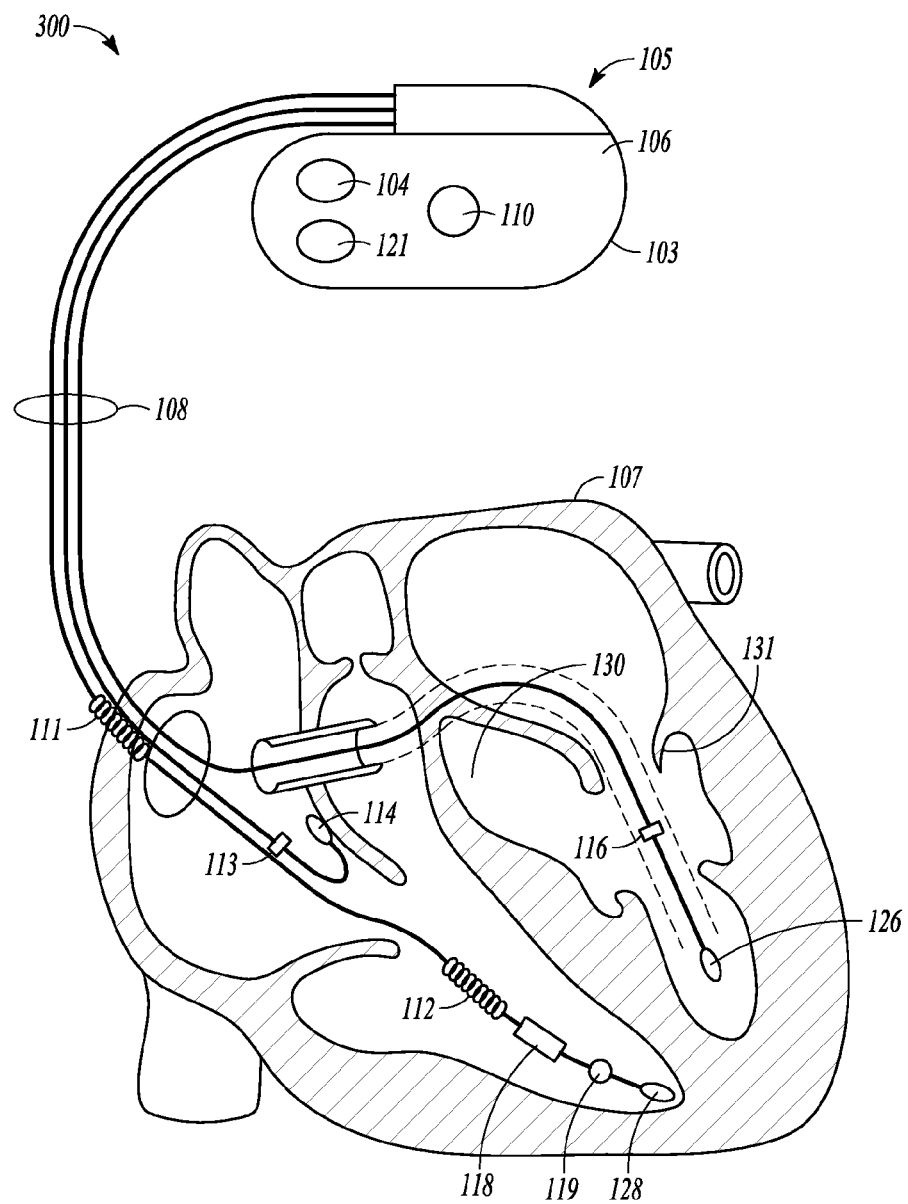
FIG. 3 illustrates generally an example that can include an implantable medical device and an implantable lead system, including leads disposed in a heart.

FIG. 3 illustrates generally an example of a system 300 that can include the IMD 105. The IMD 105 can include an implantable electronics unit 106, such as can include a processor circuit 110, a motion detector 104, or a drive/sense circuit 121. In an example, the implantable electronics unit 106 can include a housing 103 (or attached header) that can include one or more conductive portions that can optionally serve as an electrode (e.g., a "can" or "header" electrode), or the electronics unit 106 can be electrically and physically coupled to an implantable lead system 108.

Portions of the implantable lead system 108 can be inserted into a patient's thorax, such as intravascularly into or epicardially onto a patient heart 107. For example, the implantable lead system 108 can include one or more cardiac pace/sense electrodes (e.g., one or more of the electrodes 113, 114, 116, 118, 126, or 128, among others), such as can be positioned in, on, or about one or more heart chambers such as can be configured to sense one or more electrical signals from the patient heart 107. Intracardiac sensing and pacing electrodes, such as those shown in FIG. 3, can be used to sense or pace one or more chambers of the heart, such as the left ventricle (LV), the right ventricle (RV), the left atrium (LA), or the right atrium (RA).

In an example, the implantable lead system 108 can include one or more defibrillation electrodes (e.g., coil electrodes 111 and 112), such as for delivering defibrillation or cardioversion shocks to the heart 107, or for sensing one or more intrinsic electrical signals from the heart 107. In an example, the tip electrode 128 can be used to receive right ventricular electrogram information. Other defibrillation electrodes can be used to receive electrical activity information (e.g., electrograms) corresponding to one or more other portions of the heart 107.

The implantable lead system 108 and the electronics unit 106 of the IMD 105 can be configured to sense a QRS complex in a cardiac signal segment. Illustrative examples of lead systems and sensing circuitry that can sense a QRS complex are described in Patangay et al., U.S. Pat. App. No. 61/491, 459 entitled "WIDE QRS DETECTOR," which is hereby incorporated by reference.

In an example, the implantable lead system 108 can include one or more other physiological sensors. For example, the implantable lead system 108 can include a pressure sensor 119, such as can be disposed on an endocardial lead to monitor hemodynamic changes, such as a variation in pressure within a right ventricle of the heart 107. In an example, the pressure sensor 119 can include a transducer, such as including a piezo-resistive element that can be mounted on a silicon diaphragm such as behind a compliant membrane window.

A communications circuit can be included within the housing 103 (or attached header), such as to facilitate communication between the electronics unit 106 and the external module 115. In an example, the communications circuit can facilitate unidirectional or bidirectional communication with one or more implanted, ambulatory, external, cutaneous, or subcutaneous physiologic or non-physiologic sensors, patient-input devices, or information systems.

The motion detector 104 can be used to sense patient physical activity or one or more respiratory or cardiac related conditions. In an example, the motion detector 104 can be configured to sense a patient physical activity level or chest wall movements associated with respiratory effort. In an example, the motion detector 104 can include a single-axis or multiple-axis (e.g., three-axis) accelerometer that can be located in or on the housing 103. An accelerometer can be used to provide information about changes in patient posture, respiratory information including, for example, about rales or coughing, cardiac information including, for example, S1-S4 heart sounds, murmurs, or other acoustic information. In an example, an accelerometer can be used to detect activity information about an aortic valve 130 or a mitral valve 131.

A storage circuit can be included, such as within the housing 103, such as for storing a plurality of values, such as including data trend information. In an example, the storage circuit can be used to store information about a cardiac signal, such as duration information, including information about a QRS duration, a right ventricular activation duration, or a left ventricular activation duration. In an example, a right or left ventricular activation duration can include an interval that can begin at or before an onset of a QRS complex (e.g., when a P or Q wave is indicated), and can terminate at some portion of an indication of right or left ventricular activity, such as an R-wave peak, or an R-wave amplitude that exceeds a particular threshold value, such as can be derived or specified using electrogram information associated with a right or left ventricle of the heart 107.

In an example, the drive/sense circuit 121 can be configured to generate a current that flows through body tissue, such as between an impedance drive electrode (e.g., cardiac pace/sense electrodes 113) and a can electrode on the housing 103 of the electronics unit 106. In response to such a drive or excitation signal, a voltage at an impedance sense electrode 114 relative to the can electrode can be detected, and such response voltage can change as the patient's thoracic impedance changes. The response voltage signal developed between the impedance sense electrode 114 and the can electrode can be detected by the drive/sense circuit 121. In an example, information about thoracic or cardiac impedance can be used to determine, among other things, heart rate or other cardiac activity information. Locations or combinations of sense or drive electrodes other than those illustrated in FIG. 3 are possible.

Figure 4:
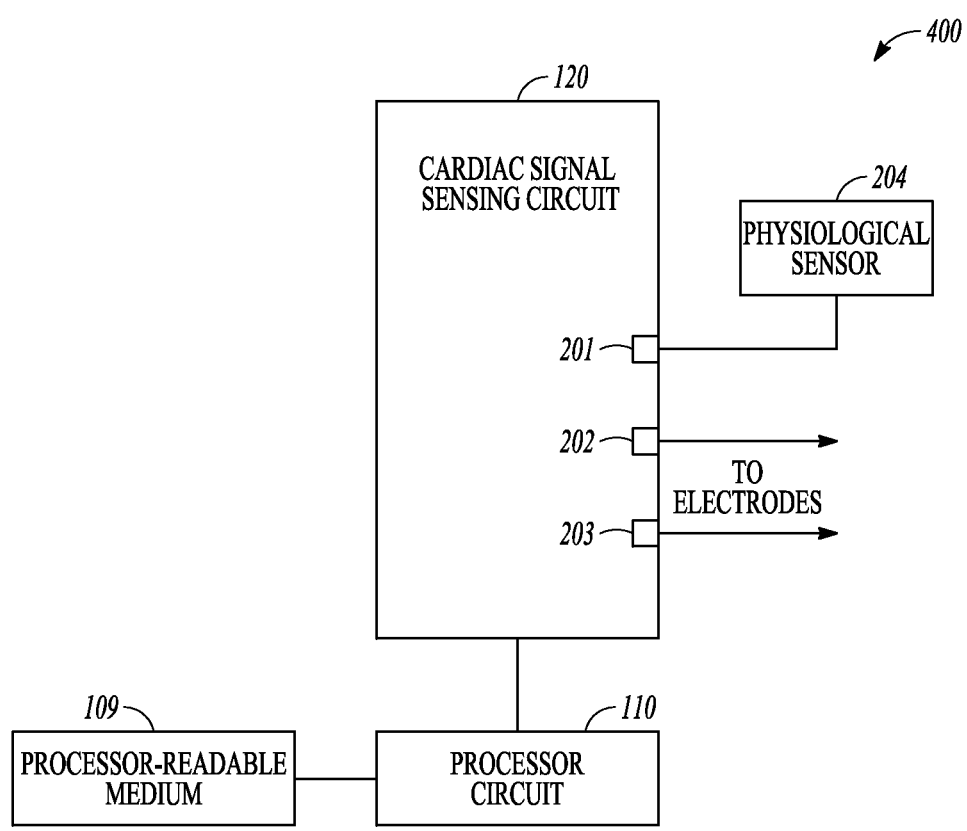
FIG. 4 illustrates generally an example of a system that can include a processor circuit, a processor-readable medium, and a cardiac signal sensing circuit.

FIG. 4 illustrates generally an example of a system 400 that can include a processor circuit 110, a processor-readable medium 109, and a cardiac signal sensing circuit 120. In an example, the processor circuit 110 can be configured to include or access the processor-readable medium 109, such as to retrieve instructions that can be used by the processor circuit 110 such as to control the cardiac signal sensing circuit 120. In an example, the processor circuit 110 can include one or more outputs, such as can be configured to provide information to the processor-readable medium 109 or to provide information to a communication circuit (e.g., communicatively coupled with the external module 115). The processor circuit 110 can include one or more inputs, such as can be configured to receive information from the cardiac signal sensing circuit 120 or the processor-readable medium 109, among other sources.

In an example, the cardiac signal sensing circuit 120 can be configured to sense a cardiac signal segment that can include a QRS complex. The QRS complex can be analyzed, such as using the processor circuit 110. Information about the QRS complex, such as information about a width, or duration, of all or a designated other portion of the QRS complex, can be processed using the processor circuit 110, which can be configured to report or make available the information to an external device (e.g., the external module 115, an external programmer, directly to a clinician's handheld mobile device, email, etc.). In an example, the processor circuit 110 can be configured to provide the QRS information for a plurality of cardiac cycles or physical activity levels. The processor circuit 110 can count, trend, or store the QRS information, such as in a histogram. For example, the histogram can be used to store information about a number or frequency of occurrences of detected features of a QRS complex, such as a width of a designated portion of a QRS complex, or a differential relationship that can include a designated portion of a QRS complex, among other relationships.

In an example, the cardiac signal sensing circuit 120 can be electrically coupled to the implantable lead system 108, or one or more other electrodes. In an example, the cardiac signal sensing circuit 120 can include a sense amplifier, and a sampling circuit, such as can be configured to sense an electrogram signal using the implantable lead system 108.

In an example, the cardiac signal sensing circuit 120 can include a unipolar or bipolar sensing channel, such as including or coupled to a sense electrode and a reference electrode. The terms "bipolar" and "unipolar" refer to a number of electrodes that can be disposed in the vicinity of the heart. A bipolar sensing channel configuration can include two electrodes that can be in contact with the heart or are intracardiac. A unipolar configuration can include a first electrode that can be in contact with the heart, intracardiac, or generally nearer the heart than the second electrode, which can be disposed remotely from the first electrode, such as at the housing of a pectorally or abdominally implanted device. Sensing the cardiac signal segment using a unipolar sensing configuration can, in some examples, provide additional information regarding a ventricular depolarization, or other thoracic activity, as compared to using a bipolar sensing configuration.

In an example, the implantable lead system 108 can include multipolar electrode leads that can be disposed in or associated with one or more of the left or right ventricles of the heart. For example, a right ventricular lead can include a tip electrode 128, a ring electrode 118, a shock electrode 112, or one or more other electrodes. In an example, RV activation duration information can be determined using electrogram information received using a bipolar electrode configuration, such as including the tip electrode 128 and the ring electrode 118, among other bipolar configurations. In an example, the RV activation duration information can be determined using electrogram information that can be received using a unipolar electrode configuration, such as using the tip electrode 128, or the shock electrode 112, among other unipolar configurations.

In an example, the cardiac signal sensing circuit 120 can include a plurality of inputs or outputs. For example, the circuit can include a first input 201, such as can be coupled to a physiological sensor 204. The cardiac signal sensing circuit 120 can include other inputs and outputs 202, 203, such as can be coupled to one or more electrodes (e.g., the implantable lead system 108) that can be configured to deliver electrostimulation therapy or to receive information about cardiac electrical activity (e.g., an electrogram signal).

In an example, the cardiac signal sensing circuit 120 can be configured to receive electrical information from in or near the heart, for example, over at least a portion of a cardiac or respiratory cycle, such as using one or more of the physiological sensor 204 or the electrodes coupled to the inputs and outputs 202, 203, among other sensors. In an example, the electrical information can include an impedance waveform, an electrical cardiogram (ECG) signal (e.g., an evoked response, a subcutaneous ECG, or other signal), an electrical signal from a heart sound sensor such as a microphone, an electrical signal from an accelerometer configured to provide an indication of mechanical cardiac activity, an electrical signal from a pressure sensor configured to provide an indication of a pressure, such as a central venous pressure (CVP), a right ventricle pressure, a coronary vein pressure, or one or more other electrical signals indicative of cardiac information.

In an example, the processor circuit 110 can include a peak detector circuit, a QRS complex duration timer circuit, or a bundle branch block (BBB) detector circuit, among others. In an example, the processor circuit 110 can use the peak detector circuit to determine a time of a maxima and a time of a minima in a sensed cardiac signal segment, such as during an identified QRS complex.

In an example, the processor circuit 110 can be configured to identify a duration of a QRS complex. For example, the circuit can identify at least a Q time in a cardiac signal segment, and can identify an S time in the cardiac signal segment. In an example, the processor circuit 110 can determine a time duration of the QRS complex in the cardiac signal segment using the identified Q time and S time.

In an example, the Q time can be identified using the processor circuit 110 to determine an isoelectric amplitude value of the cardiac signal segment. Isoelectric amplitude values can be determined from sampled values of the sensed cardiac signal segment, and an isoelectric value of the signal can be defined to be zero volts or an amplitude of a substantially "flat" portion of the cardiac signal segment. In an example, the processor circuit 110 can identify, as a Q time in the QRS complex, a time at which the cardiac signal segment amplitude deviates from the isoelectric amplitude value by at least a specified threshold deviation value.

To identify the S time, in an example, the processor circuit 110 can be configured to determine an isoelectric value time, after the determined maxima and minima times, when the cardiac signal segment returns to the same or a different isoelectric amplitude value. In an example, the S time in the QRS complex can be identified as the time that follows both the determined maxima and minima times and precedes the isoelectric value time. In an example, the cardiac signal segment amplitude at the identified S time can satisfy a specified amplitude change criterion from an isoelectric amplitude value. Examples of identifying an S time are described in Patangay et al., U.S. Pat. App. No. 61/491,459, which is incorporated by reference.

In an example, the processor circuit 110 can be configured to determine one or more portions of the QRS complex. For example, the processor circuit 110 can be configured to determine a Q-RV interval, such as an RV activation duration. The duration information can be used to determine an abnormal cardiac signal morphology, such as by comparing a portion of the QRS complex (e.g., the Q-RV interval) to an overall QRS complex duration. Methods of identifying various cardiac signal morphologies are further described below, such as in the discussion of FIGS. 7 through 11.

Figure 5A:
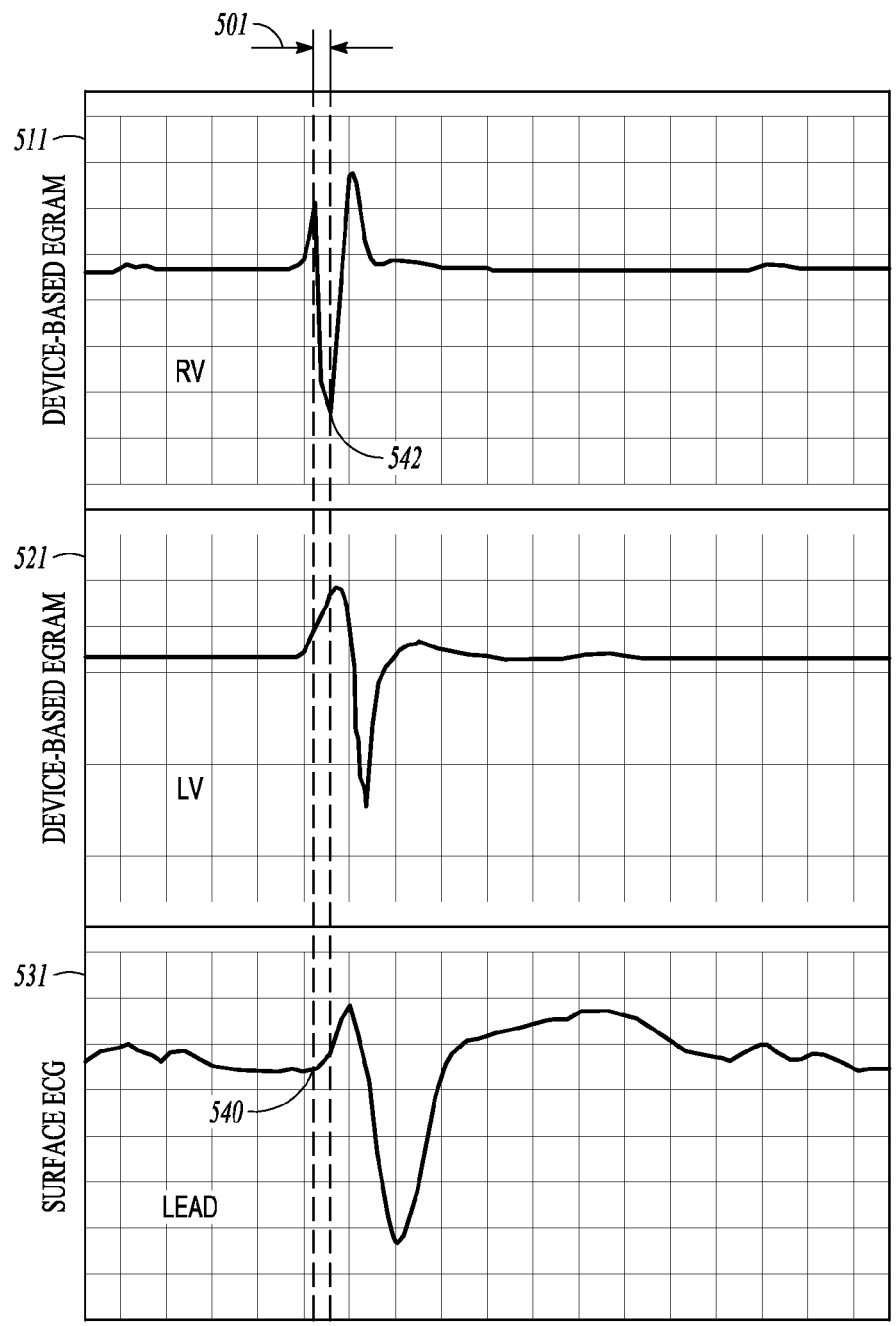
FIGS. 5A and 5B illustrate generally examples that can include device-based electrograms.
Figure 5B:
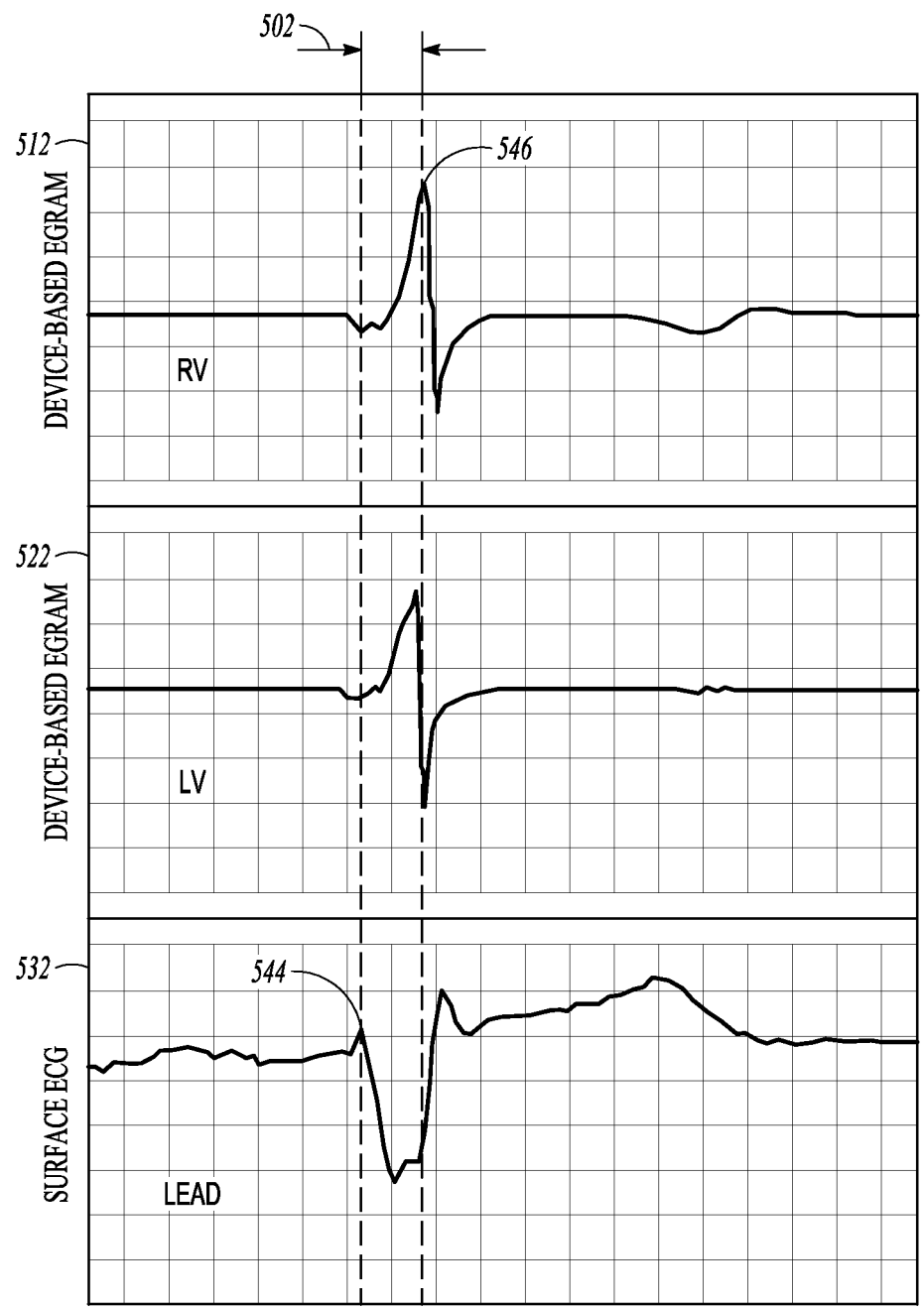

FIGS. 5A and 5B illustrate generally examples that can include device-based electrogram signals. In an example, the electrograms in FIGS. 5A and 5B can be determined such as using the system 300. FIG. 5A illustrates an example of several time-aligned electrograms that can be used to provide an indication of an abnormal cardiac signal morphology, such as a bundle branch block morphology.

In an example, the electrograms 511, 521, 531 of FIG. 5A can be obtained, such as using the IMD 105 or the system 300. In the example of FIG. 5A, the system 300 can include a right ventricular rate electrode (e.g., an electrode configured to deliver a unipolar pacing therapy to a right ventricle, such as using the tip electrode 128), or a left ventricular rate electrode (e.g., an electrode configured to deliver a bipolar pacing therapy to a left ventricle, such as using the tip electrode 126 or ring electrode 116), among others. In an example, these electrodes or others, such as together with the IMD 105, can be used to measure electrograms indicative of cardiac electrical activity (e.g., device-based electrograms). For example, the right ventricular rate electrode can be used to obtain a first RV electrogram 511, and the left ventricular rate electrode can be used to obtain a first LV electrogram 521. Any number of electrograms can be obtained and time-aligned, such as shown in FIGS. 5A and 5B, for further analysis.

In an example, other electrodes or electrode configurations can be used to obtain electrograms, such as using one or any combination of the electrodes in the implantable lead system 108. For example, the shock electrode 112 can be used to obtain a shock electrogram. In the example of FIG. 5A, an additional electrode, such as a surface electrode disposed on the patient body 101, can be used to obtain a surface ECG electrogram 531.

In an example, at least one electrogram can be used to determine an onset of a QRS complex, such as a Q time. In the example of FIG. 5A, the surface ECG electrogram 531 can be used to determine an indication of the Q time 540, such as by identifying a deviation from an isoelectric amplitude value, such as described above. Other electrograms can be used to determine the Q time 540, such as an electrogram obtained using the shock electrode 112, or an electrogram obtained using one or more other electrodes (e.g., other electrodes in the implantable lead system 108, or other surface electrodes, such as one or more electrodes used in a 12 lead ECG).

In an example, at least one electrogram can be used to determine an R-wave of the QRS complex. For example, at least one electrogram can be used to identify a feature of the R-wave, such as an onset, peak, or inflection point, among other features, of the R-wave. In the example of FIG. 5A, the first RV electrogram 511 can be used to determine a peak 542 of the R-wave (e.g., a first dominant peak in the electrogram). In an example, the R-wave or R-wave feature can be identified using one or more of electrograms 511, 521, or 531, such as using the processor circuit 110. In an example, the same electrogram can be used to identify the onset of a QRS complex (e.g., a Q time) and the R-wave or feature of the R-wave.

In an example, the duration of a QRS complex or a portion of a QRS complex can be used to provide an indication of cardiac dysfunction. For example, a QRS complex can provide information representative of both right and left sides of the myocardium, and, where the QRS complex is wide, or extended in duration relative to a normal QRS complex, particular portions of the myocardium that are delayed relative to the other portions can be identified. For example, where right ventricular activation occurs normally relative to a wide QRS complex, LBBB can be indicated.

In an example, the processor circuit 110 can be used to identify a Q-RV interval 501 as a period beginning at the Q time 540 and ending at the R-wave peak 542. In an example, the Q-RV interval 501 can provide an indication of a cardiac ventricular dysfunction when the interval is less than a particular threshold duration. In the example of FIG. 5A, the Q-RV interval 501 can be about 13 ms, and can indicate LBBB where the overall QRS complex duration is extended, or wide, relative to a normal patient state (e.g., a QRS complex duration that exceeds about 100 ms).

FIG. 5B illustrates generally several electrograms that can be used to provide an indication of an abnormal patient cardiac morphology, such as right bundle branch block (RBBB) or an intraventricular conduction delay (IVCD) morphology. IVCD can be any non-specific block, such as may affect both sides of the myocardium. In an example, the electrograms of FIG. 5B can be obtained, such as according to the description of FIG. 5A, or they can be obtained using different electrode configurations. In the example of FIG. 5B, the electrograms can include a second RV electrogram 512, a second LV electrogram 522, or a second surface ECG electrogram 532.

As described above, any one of the electrograms 512, 522, or 532, among other electrograms, can be used to identify an onset of a QRS complex, or can be used to identify an R-wave or a portion of an R-wave, such as an R-wave feature (e.g., peak, inflection point, threshold amplitude, etc.). In the example of FIG. 5B, the second surface ECG electrogram 532 can be used to determine an indication of the Q time 544, and the second RV electrogram 512 can be used to determine an indication of the R-wave peak 546.

In an example, the processor circuit 110 can be used to identify a second Q-RV interval 502. The second Q-RV interval 502 can be a period beginning at a time corresponding with the Q time 544 and ending at a time corresponding with the R-wave peak 546. In an example, the Q-RV interval 502 can provide an indication of RBBB or IVCD when the interval is greater than a threshold duration. In the example of FIG. 5B, the Q-RV interval 502 can be about 87 ms, and can indicate RBBB or IVCD where the overall QRS complex duration is extended, or wide, relative to a normal QRS width.

In an example, a QRS complex, QRS duration, or a portion of the QRS duration (e.g., an RV or LV activation duration) can be determined using other physiological sensors 204 (e.g., sensors configured to provide information other than electrogram signal information), such as can be configured to provide heart sound information, or other information indicative of heart tissue or valve activity. In an example, a point other than a Q time can be used as a reference point, such as for determining an RV or LV activation duration. For example, an accelerometer can be used to receive information about an AV valve closure (e.g., corresponding to an R-wave peak in an electrogram), or to receive information about a mitral or aortic valve opening or closing (e.g., to indicate an S1 or S2 heart sound, respectively). One or more of these fiducial points, among others, can be used to indicate a Q time or similar reference point, such as in combination with electrogram information. In an example, an RV activation duration can be representative of a time duration between at least one of (1) an aortic valve or mitral valve closure and (2) an R-wave peak. In an example, the valve closures can be indicated using one or more heart sound sensors, and the R-wave peak can be identified in an right ventricular electrogram.

Figure 6:
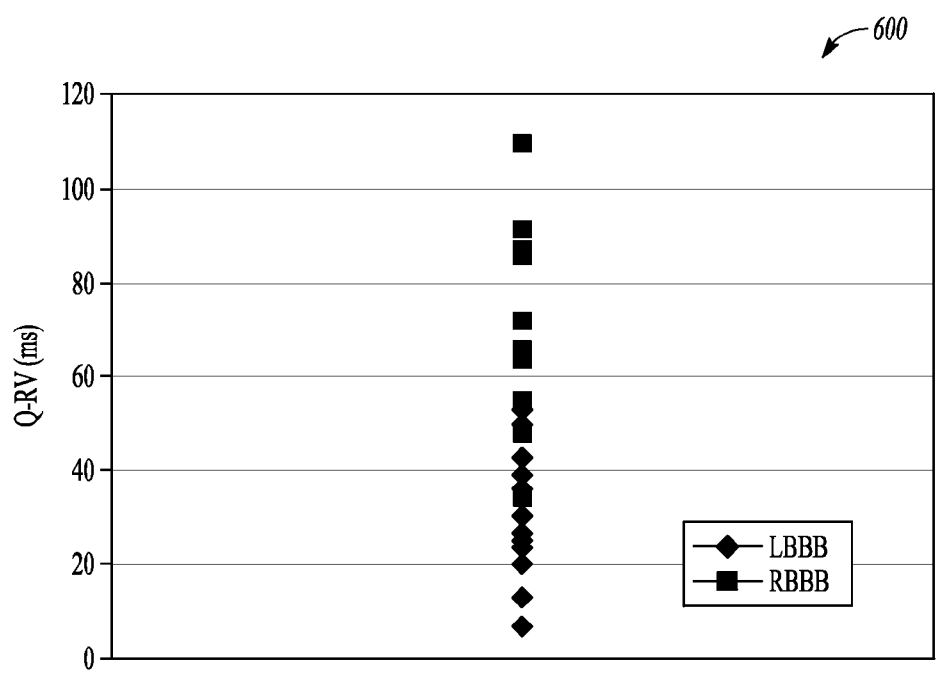
FIG. 6 illustrates generally an example of Q-RV interval information from several patients.

FIG. 6 illustrates generally an example of Q-RV interval information from about 30 patients. The Q-RV interval information in the example of FIG. 6 was obtained using an external 12 lead ECG. As shown in the example of FIG. 6, patients with LBBB tend to have a Q-RV interval of about 10 to 50 ms, and patients with RBBB or IVCD tend to have a Q-RV interval of about 50 to 120 ms. Therefore, by identifying a patient's Q-RV interval, such as relative to an overall QRS complex width, patients with dysfunctional cardiac conduction morphologies can be identified.

Figure 7:
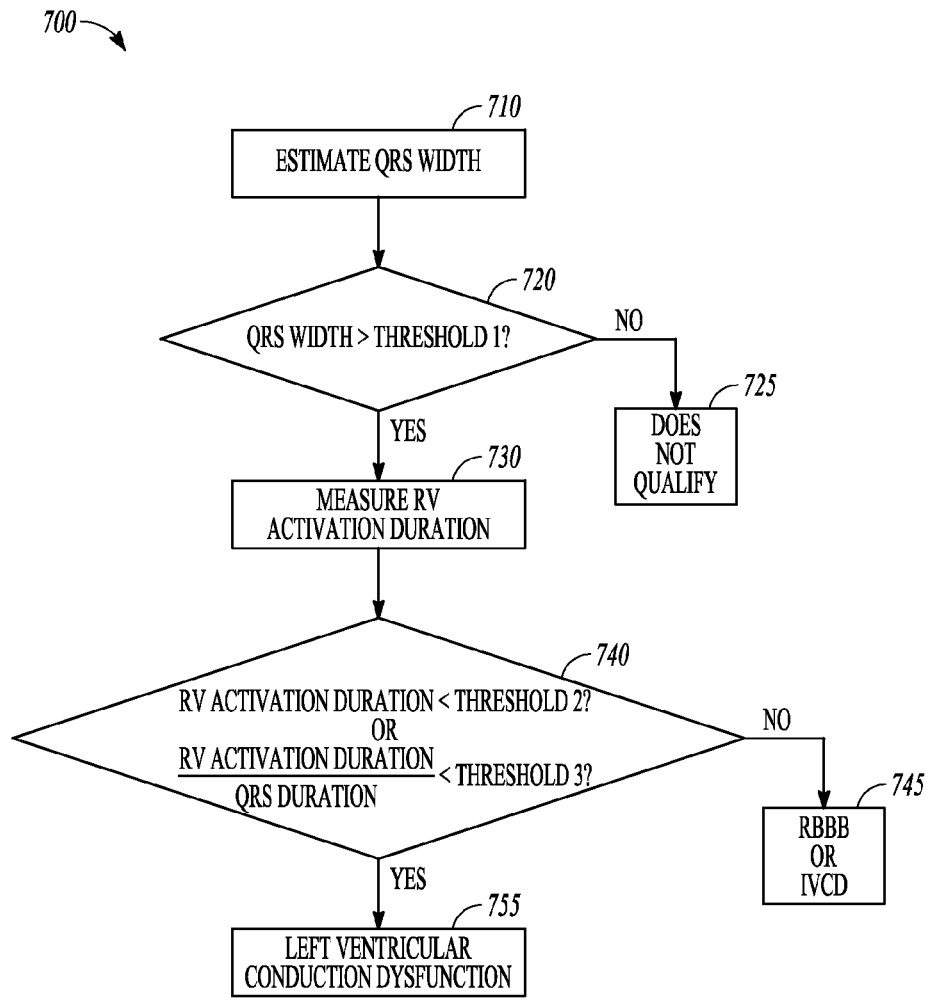
FIG. 7 illustrates generally an example that can include identifying left ventricular conduction dysfunction.

FIG. 7 illustrates generally an example 700 that can include identifying left ventricular conduction dysfunction. For example, FIG. 7 illustrates generally how information derived from an electrogram, such as can be obtained using an electrode coupled to an implantable cardioverter-defibrillator or other device, can be used to determine if a patient exhibits a left bundle branch block cardiac signal morphology. For example, a left bundle branch block can be indicated using a relative comparison of a right ventricular activity indication and a portion of a QRS complex duration. In an example, identifying a left bundle branch block can indicate that the patient is a candidate for a cardiac resynchronization therapy device.

In an example, at 710, a QRS width can be estimated, such as using one or more of the techniques described above in the discussion of FIG. 5A, among others. In an example, a cardiac signal (e.g., an electrogram) can be received using the cardiac signal sensing circuit 120. The QRS width estimation can be performed using the processor circuit 110 to identify an interval between a Q time and S time of the cardiac signal. In an example, the QRS width can be estimated from previously-recorded patient data.

At 720, the estimated QRS width can be compared to a first threshold value to determine if the QRS complex is extended relative to a normal patient QRS complex width, such as using the processor circuit 110. A normal patient QRS complex width can generally be less than about 100 ms. In an example, if the QRS complex does not exceed the first threshold value, then the patient can be identified as not an ideal candidate for cardiac resynchronization therapy, at 725. For example, the patient can be identified as being at low risk for LBBB, RBBB, or IVCD, or other dysfunction associated with extended QRS width.

In an example, the first threshold value can be determined using patient-specific information, such as using QRS complex duration information obtained from a patient chart (e.g., using information about a previously-acquired ECG) or electronic medical record (EMR). In an example, the first threshold value can be more than about 100 ms, such as about 120 ms.

In an example, the QRS width can exceed the first threshold value, such as can be determined using the processor circuit 110. A right ventricular (RV) activation duration, or Q-RV interval, can be measured at 730, such as according to the discussion of FIGS. 5A and 5B, above. For example, the processor circuit 110 can be used to analyze an electrogram to identify the RV activation duration. In an example, the RV activation duration can be determined using previously-recorded patient data.

At 740, the RV activation duration can be analyzed, such as using the processor circuit 110. In an example, the RV activation duration can be compared to a second threshold value (e.g., a threshold value specified to be between about 40 and 50 ms). In an example, the second threshold value can be determined using patient-specific information, such as using QRS complex duration information obtained from a patient. If the RV activation duration exceeds the second threshold value, RBBB or IVCD can be indicated at 745. If the RV activation duration does not exceed the second threshold value, a left ventricular conduction dysfunction, such as LBBB, can be indicated at 755.

In an example, at 740, a ratio or other relative indication of the RV activation duration to a QRS duration can be compared to a third threshold value. If the ratio exceeds the third threshold value, RBBB or IVCD can be indicated at 745. If the ratio does not exceed the third threshold value, or the RV activation duration is less than the second threshold value, then LBBB can be indicated at 755. In an example, the second threshold value can be specified to be about 45 ms, and the third threshold value can be specified to be between about 0.2 and 0.4. Other specified threshold values can be used as well, such as corresponding to a particular patient cardiac morphology. In an example, the third threshold value can be specified using previously-acquired patient data, such as patient-specific data including information about a patient RV activation duration or a patient QRS width.

In an example, the RV activation duration measured at 730 can be used to provide an indication of RBBB or IVCD. In an example, the indication of RBBB or IVCD can be provided without using information about the overall patient QRS width. For example, where the RV activation duration is extended relative to a normal RV activation duration, RBBB or IVCD can be indicated. In an example, the normal activation duration can be determined using other, previously-acquired patient data, such as patient-specific data including information obtained from an external 12 lead ECG.

In an example, at least one of the IMD 105 or the external module 115 can be used to provide an alert or indication, such as that a patient is at low risk for LBBB, RBBB, or IVCD (e.g., at 725), to provide an alert or indication that a patient exhibits an RBBB or IVCD morphology, or to provide an alert or indication that a patient exhibits left ventricular conduction dysfunction. For example, the alert or indication can be provided to a user, such as the patient or a clinician, such as according to the discussion of FIG. 1, above. In an example, one or more therapies, such as an electrostimulation or drug therapy, can be triggered in response to an identification of RBBB or IVCD at 745, or an identification of left ventricular conduction dysfunction at 755.

Figure 8:
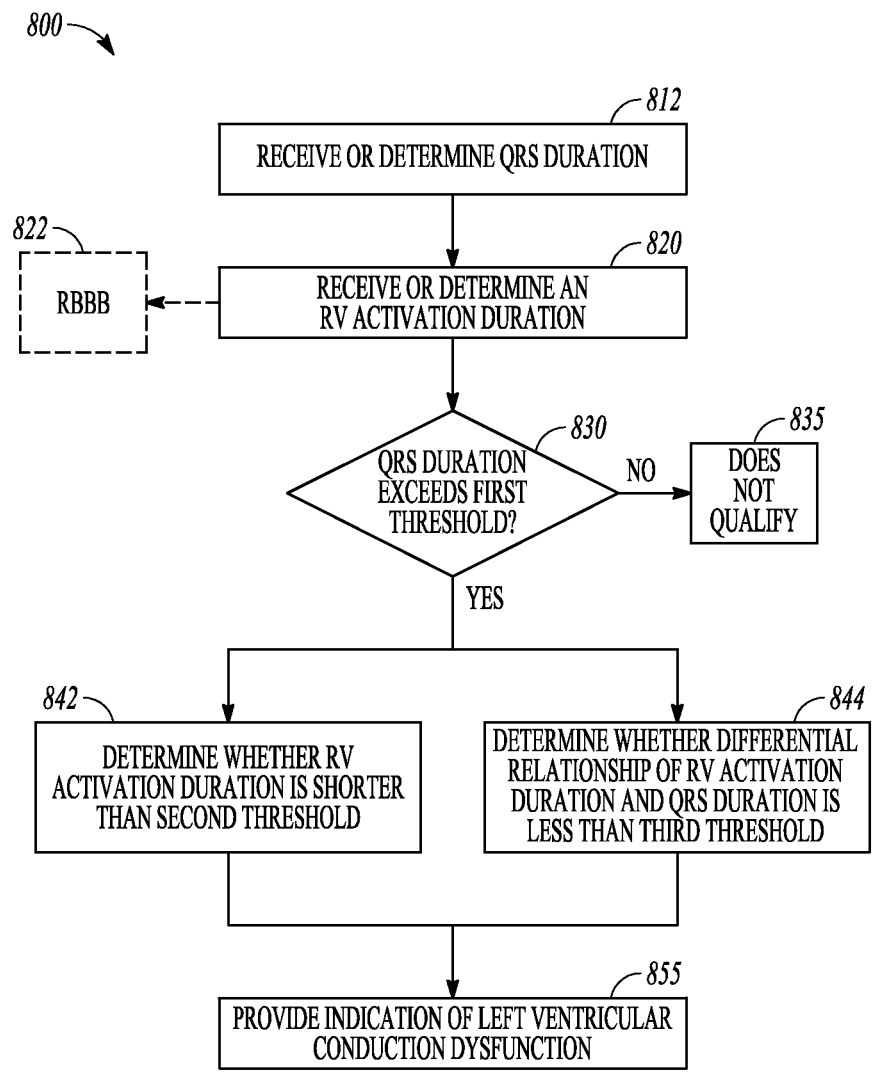
FIG. 8 illustrates generally an example that can include identifying left ventricular conduction dysfunction.

FIG. 8 illustrates generally an example 800 that can include providing an indication of a left ventricular conduction dysfunction. In the example of FIG. 8, at 812, information about a QRS duration can be received or determined. In an example, at 820, an RV activation duration can be received or determined, such as before determining whether the QRS duration exceeds a first threshold value at 830. Accordingly, the example of FIG. 8 can be used to provide an indication of RBBB at 822, such as before performing the comparison at 830. In an example, the information about the QRS duration and the RV activation duration can be received or determined according to the discussion of FIG. 7, above.

In an example, the RV activation duration can be compared to a second threshold value at 842, such as according to the discussion at 740. If the RV activation duration does not exceed the second threshold value (e.g., 45 ms), an indication of left ventricular conduction dysfunction (e.g., LBBB) can be provided at 855.

In an example, a differential relationship between the RV activation duration and the QRS duration can be determined at 844. The differential relationship can include, among other relationships, a ratio or a difference of the RV activation duration and the QRS duration. In an example, at 844, the differential relationship can be compared to a third threshold value and, if the differential relationship is less than the third threshold value, an indication of a left ventricular conduction dysfunction (e.g., LBBB) can be provided.

Figure 9:
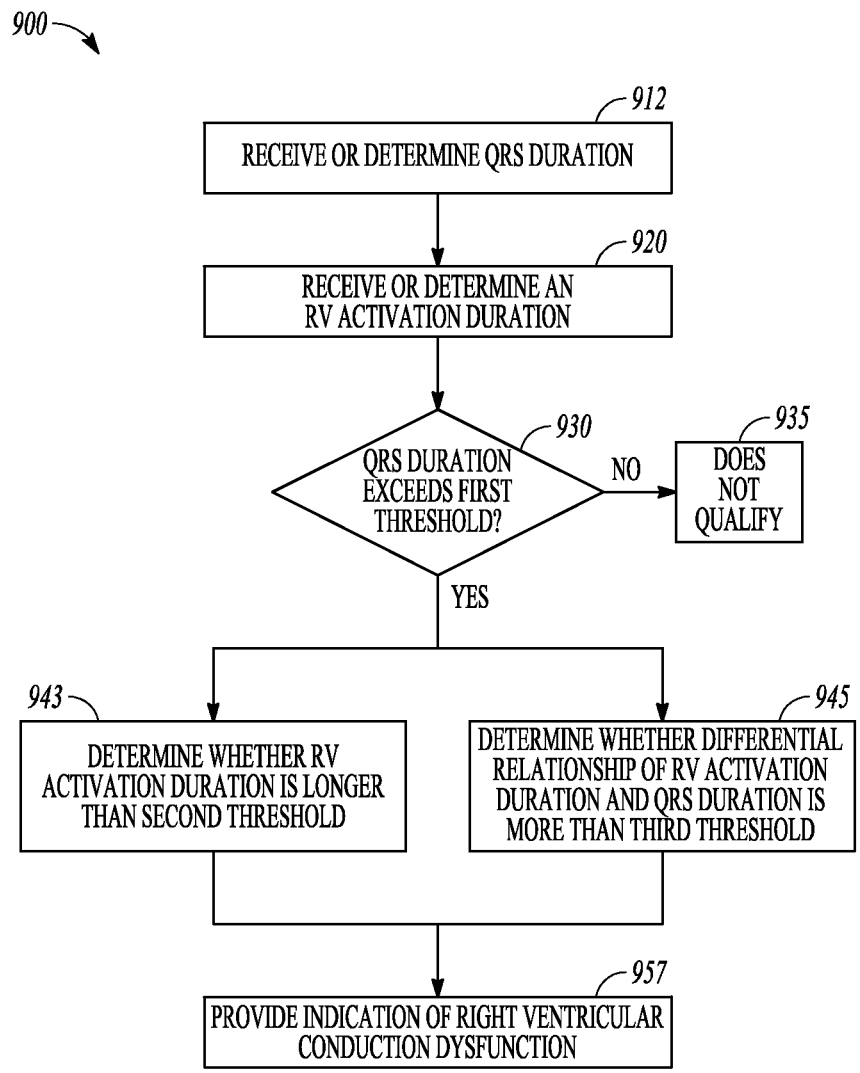
FIG. 9 illustrates generally an example that can include identifying right ventricular conduction dysfunction.

FIG. 9 illustrates generally an example 900 that can include providing an indication of a right ventricular conduction dysfunction. In the example of FIG. 9, at 912, information about a QRS duration can be received or determined. In an example, an RV activation duration can be received or determined at 920, such as using the information about the QRS duration received at 912. For example, the information about the QRS duration can be determined using an electrogram, such as can be received using a shock electrode disposed in the heart 107. The information about the QRS duration and the RV activation duration can be determined such as by analyzing the electrogram, such as according to the discussion of FIGS. 5A and 5B.

In an example, such as shown in FIG. 9, the QRS duration (e.g., obtained at 912) can be compared to a first threshold value at 930. If the QRS duration exceeds the first threshold value (e.g., about 120 ms), then the RV activation duration can undergo further analysis. In an example, if the QRS duration does not exceed the first threshold value, a normal patient QRS width can be indicated and the analysis can terminate.

In an example, such as shown in FIG. 9, the RV activation duration can be compared to a second threshold value at 943, and, when the RV activation duration exceeds the second threshold value, an indication of a right ventricular conduction dysfunction can be provided at 957. In an example, the right ventricular conduction dysfunction can include RBBB or IVCD.

In an example, at 945, a differential relationship between the RV activation duration and the QRS duration can be determined (e.g., a ratio of the RV activation duration to the QRS duration). The differential relationship can be compared to a third threshold value. In an example, at 957, if the differential relationship exceeds the third threshold value (e.g., where the differential relationship is a ratio of the RV activation duration to the QRS duration, the third threshold value can be selected to be about 0.3), an indication of right ventricular conduction dysfunction can be provided.

In an example, the indication of right ventricular conduction dysfunction provided at 957 can be provided even if information about a QRS duration is not available. For example, the information about the RV activation duration, such as received or determined at 920, can be used to identify RBBB or IVCD patients.

Figure 10:
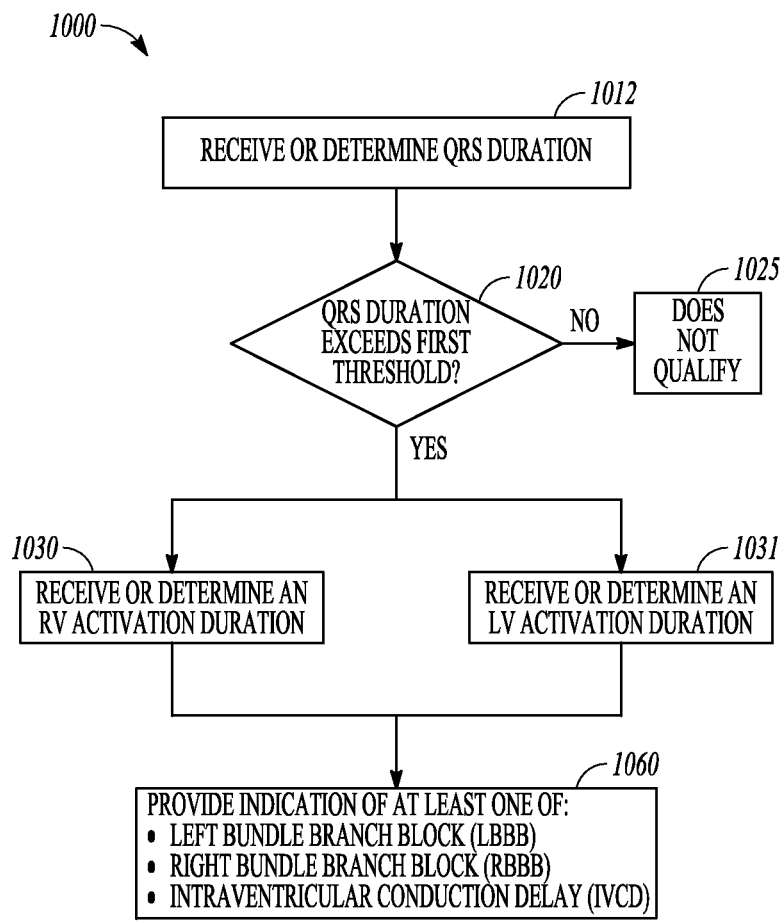
FIG. 10 illustrates generally an example that can include providing an indication of cardiac conduction dysfunction.

FIG. 10 illustrates generally an example 1000 that can include providing an indication of at least one of left bundle branch block, right bundle branch block, or intraventricular conduction delay. In an example, information about a QRS duration can be received or determined at 1012, such as according to the discussion of FIG. 7. The QRS duration can be compared to a first threshold value at 1020, such as according to the discussion of FIG. 7 at 720.

In an example, an RV activation duration can be determined at 1030. The RV activation duration can be compared to one or more threshold values, and the comparison can be used to provide, among other things, an indication of at least one of LBBB, RBBB, or IVCD. In an example, the indication of at least one of RBBB or IVCD can be provided when (1) the QRS duration exceeds the first threshold value, and (2) the RV activation duration exceeds a second threshold value. In an example, the indication of LBBB can be provided when (1) the QRS duration exceeds the first threshold value, and (2) the RV activation duration is less than the second threshold value.

In an example, an LV activation duration can be determined at 1031. The LV activation duration can be determined using one or more electrodes disposed in association with the left ventricle of the heart 107, such as in a patient having an implantable cardiac resynchronization therapy device coupled to a left ventricular lead. The LV activation duration can be compared to one or more specified threshold values, and the comparison can be used to provide, among other things, an indication of LBBB. In an example, information about the LV activation duration can be used for other patient screening, diagnostic, or therapy control, such as to indicate if a patient is non-responsive to therapy, if a patient cardiac conduction pattern has changed, or for other screening, diagnostic, or therapy control purpose. For example, information about the LV activation duration can be used to identify a cardiac signal morphology or a change in a cardiac signal morphology, such as can be used to detect an ischemic episode. In an example, the LV and RV activation durations can be used, at 1060, such as together with information about the QRS duration, such as to provide an indication of one or more of LBBB, RBBB, or IVCD.

In an example, RV or LV activation duration information can be determined using electrogram information that can be received using multipolar electrode leads. For example, a multipolar electrode lead disposed in or near a right ventricle can be configured to receive information from multiple bipolar or unipolar sensing configurations. In an example, two or more electrograms can be used to determine at least one of an RV or LV activation duration. For example, using more than one electrogram can improve the accuracy of a bundle branch block or IVCD indication, or can be used to better characterize a patient cardiac signal morphology, such as using electrogram signals received from multiple locations in or near the heart 107.

In an example, first RV electrogram information can be received using a bipolar configuration comprising the ring electrode 118 and the tip electrode 128. Concurrently, second RV electrogram information can be received, such as using a second bipolar configuration, or using a unipolar configuration, such as comprising a second ring electrode and a can electrode (e.g., a conductive portion of the housing 103). In an example, the first and second RV electrogram information can be compared, such as to verify that specified features (e.g., an R-wave peak) of the first and second RV electrograms correspond, such as in time or in magnitude. For example, where one electrogram indicates an erratic or unexpected electrogram or electrogram feature, an indication can be provided, such as using the external module 115, to alert a patient or clinician of an issue with an implanted lead or some other component of the system 300. In an example, QRS duration information or RV activation information, among other information, can be determined using each of the first and second electrograms, among others, and the information can be compared, averaged, or otherwise analyzed, such as prior to performing any of the examples of FIGS. 7-11. In an example, any number of electrograms or other ECG information can be obtained and compared to verify or further analyze QRS duration information or RV or LV activation duration information.

In an example, the processor circuit 110 can be configured to receive multiple signals or electrograms from one or more multipolar electrode leads (e.g., in the implantable lead system 108). For example, information about a cardiac activation sequence can be detected using the multipolar leads, such as using leads disposed in the left and right ventricles of the heart 107. The information about the cardiac activation sequence can be used to characterize a cardiac morphology, such as to provide an indication of BBB or IVCD. For example, a first lead can be disposed in or near the right ventricle, and can receive an indication of right ventricular cardiac activity at a first time. An indication of left ventricular cardiac activity can be received at a second time, such as using a second lead disposed in or near the left ventricle. In an example, a difference or differential relationship between the first and second times can be used to provide the indication of BBB or IVCD.

Figure 11A:
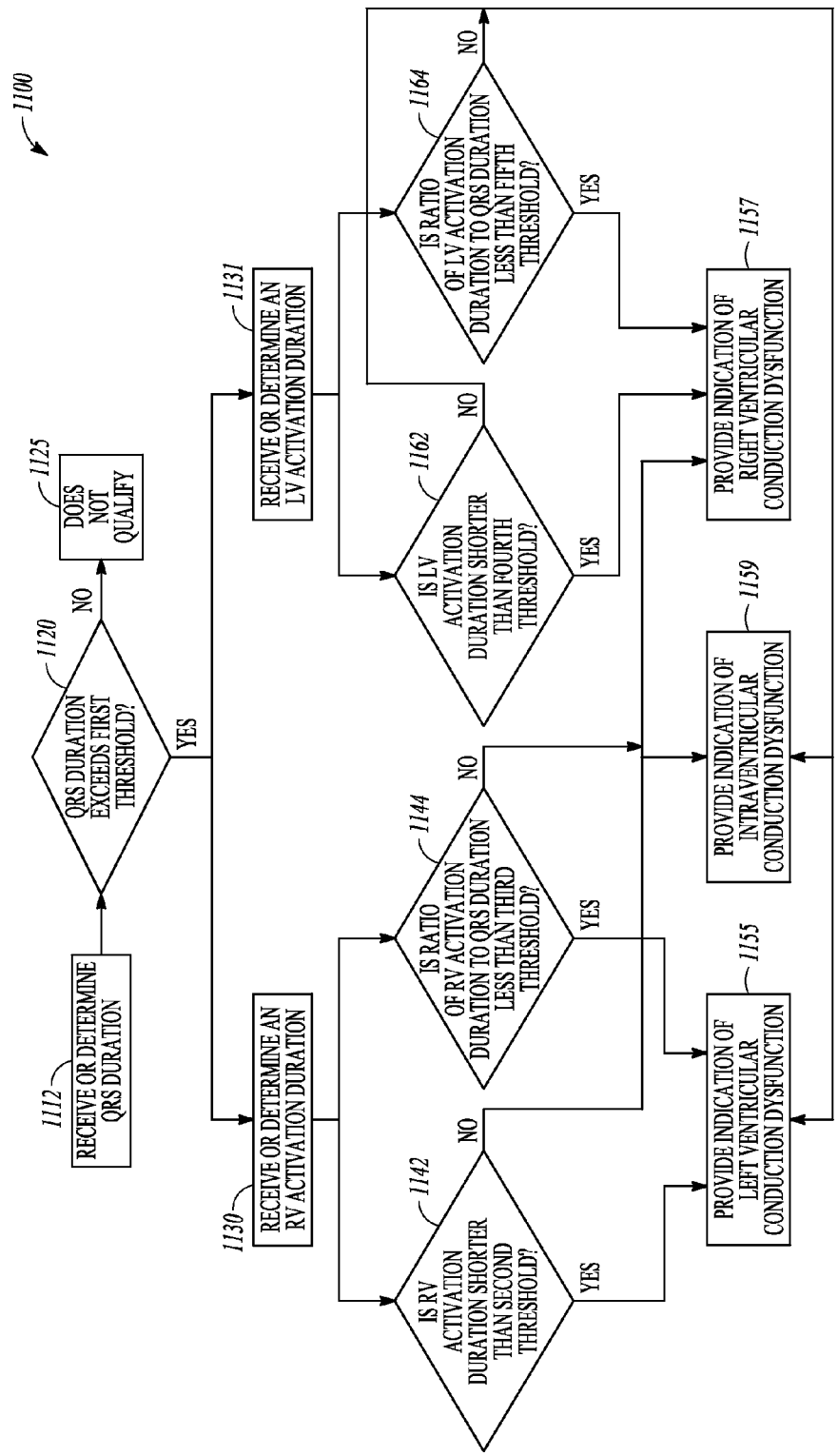
FIGS. 11A and 11B illustrate generally examples that can include providing an indication of cardiac conduction dysfunction.

FIG. 11A illustrates generally an example 1100 that can include providing an indication selected from a group that includes candidate indications of left ventricular conduction dysfunction, right ventricular conduction dysfunction, or intraventricular conduction dysfunction. In an example, a QRS duration, and at least one of an RV activation duration or an LV activation duration, can be received or determined, such as at 1112, 1130, and 1131, such as according to the discussion of FIG. 10, above.

In an example, the RV activation duration can be used, such as together with information about a QRS duration, to provide an indication of left ventricular conduction dysfunction at 1155, such as according to the discussion of FIG. 8. In an example, at least one of the RV activation duration, or the ratio or other differential relationship of the RV activation duration to the QRS duration, can be compared to corresponding second and third threshold values, such as at 1142 and 1144, respectively. In an example, when the RV activation duration is shorter than the second threshold value, or when the ratio of the RV activation duration to the QRS duration is less than the third threshold value, an indication of left ventricular conduction dysfunction can be provided at 1155.

In an example, an indication of intraventricular conduction dysfunction can be provided at 1159. For example, when the RV activation duration is not shorter than the second threshold value, or when the ratio of the RV activation duration to the QRS duration is not less than the third threshold value, an indication of intraventricular conduction dysfunction can be provided at 1159.

In an example, an indication of right ventricular conduction dysfunction can be provided at 1157. For example, when the RV activation duration is not shorter than the second threshold value, or when the ratio of the RV activation duration to the QRS duration is not less than the third threshold value, an indication of right ventricular conduction dysfunction can be provided at 1157.

In an example, the LV activation duration can be used, such as together with information about a QRS duration, to provide an indication of left ventricular conduction dysfunction at 1155. In an example, at least one of the LV activation duration, or the ratio of the LV activation duration to the QRS duration, can be compared to corresponding fourth and fifth threshold values, such as at 1162 and 1164, respectively. In an example, when the LV activation duration is not shorter than the fourth threshold value, or when the ratio of the LV activation duration to the QRS duration is not less than the fifth threshold value, an indication of left ventricular conduction dysfunction can be provided at 1155.

In an example, an indication of intraventricular conduction dysfunction can be provided at 1159. For example, when the LV activation duration is not shorter than the fourth threshold value, or when the ratio of the LV activation duration to the QRS duration is not less than the fifth threshold value, an indication of intraventricular conduction dysfunction can be provided at 1159.

In an example, an indication of right ventricular conduction dysfunction can be provided at 1157. For example, when the LV activation duration is shorter than the fourth threshold value, or when the ratio of the LV activation duration to the QRS duration is less than the fifth threshold value, an indication of right ventricular conduction dysfunction can be provided at 1157.

Figure 11B:
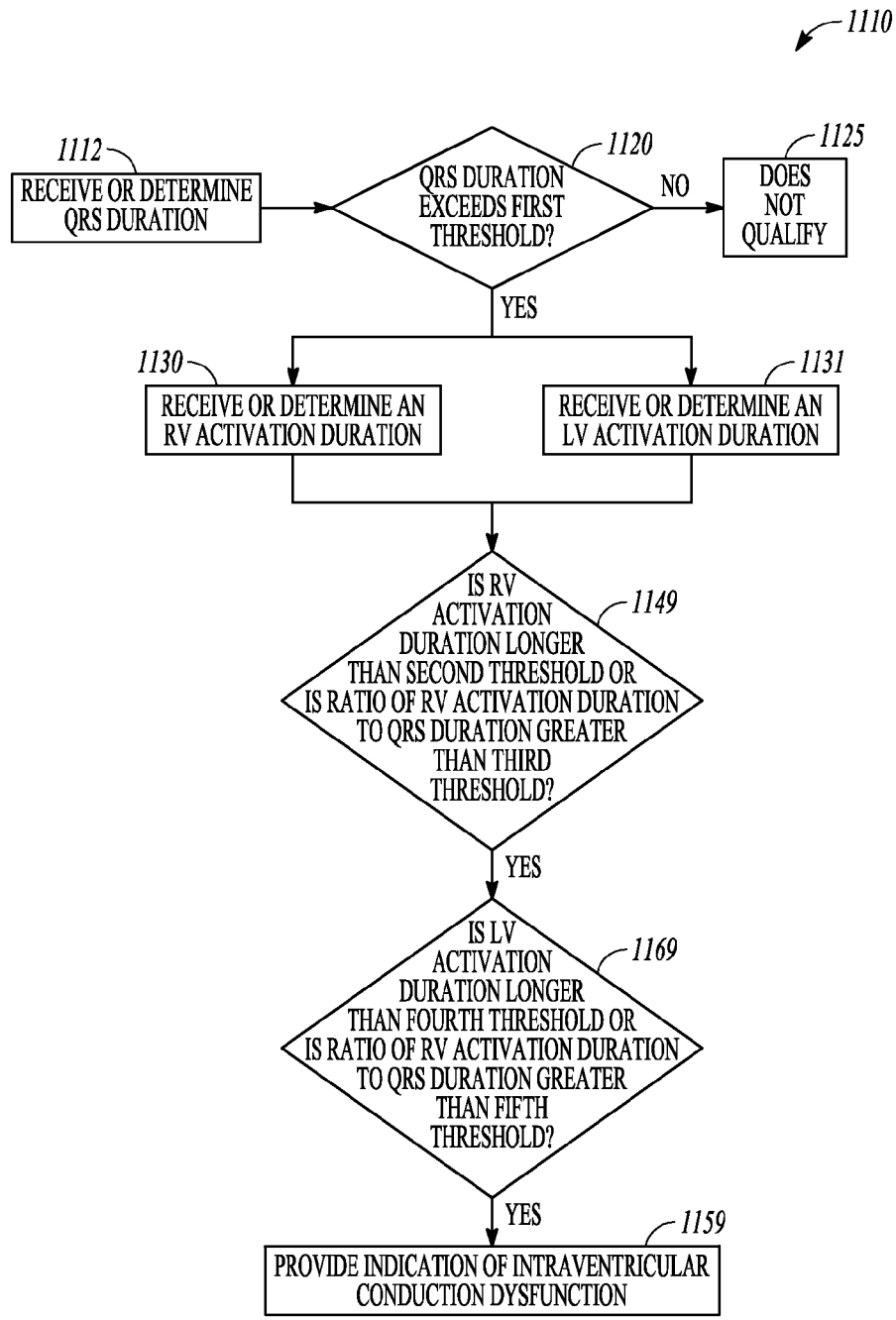

FIG. 11B illustrates generally an example 1110 that can include providing an indication of intraventricular conduction dysfunction. In an example, a QRS duration, and LV and RV activation durations, can be received or determined, such as at 1112, 1130, and 1131, such as according to the discussion of FIG. 10, above.

In an example, the indication of intraventricular conduction dysfunction can be provided at 1159 when at least first and second conditions are met. The first condition can be determined at 1149. If the RV activation duration is greater than a second threshold value, or if the ratio of the RV activation duration to the QRS duration is greater than a third threshold value, the first condition can be satisfied.

The second condition can be determined at 1169. If the LV activation duration is greater than a fourth threshold value, or if the ratio of the LV activation duration to the QRS duration is greater than a fifth threshold value, the second condition can be satisfied. In an example in which both the first and second conditions are satisfied (i.e., at 1149 and 1169), an indication of intraventricular conduction dysfunction can be provided at 1159.

Figure 12:
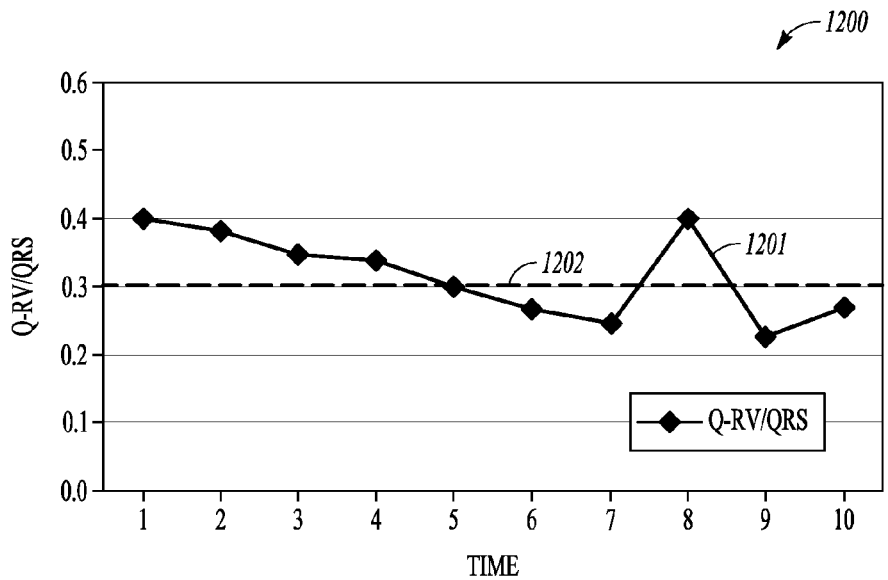
FIG. 12 illustrates generally an example of monitoring an indication of a patient cardiac status.

FIG. 12 illustrates generally an example that can include monitoring an indication of a patient cardiac status. In an example, a chart 1200 can include a trendline 1201 that can be used to track a ratio or other differential relationship of a patient Q-RV interval to the patient QRS duration, such as over multiple cardiac cycles or other periods (e.g., the periods 1 through 10 indicated on the chart 1200). In an example, the trendline 1201 can indicate the ratio at discrete times.

In an example, such as shown in FIG. 12, a ratio of a patient Q-RV interval to the patient QRS duration of about 0.4 can be associated with a first time, such as corresponding to an average patient Q-RV interval and QRS duration on a first day. A ratio of about 0.35 can be associated with a third time, such as corresponding to an average patient Q-RV interval and QRS duration on a third day. In an example, the time axis can correspond to intra-day Q-RV interval or QRS duration information (e.g., interval or duration information obtained every cardiac cycle, every minute, or every hour, etc.), or inter-day Q-RV interval or QRS duration information (e.g., interval or duration information obtained daily, weekly, monthly, etc.).

In an example, the IMD 105 (e.g., an implantable ICD, CRT-D, or other device) or the external module 115 can include a processor circuit (e.g., the processor circuit 110) configured to receive information about a patient Q-RV interval, the patient QRS duration, and corresponding time information. The received information can be stored in memory, such as in a histogram, and the information can be analyzed either continuously, recurrently, or periodically (e.g., daily, weekly, monthly, etc.) to detect a change in the ratio of a patient Q-RV interval to the patient QRS duration.

In an example, the trendline 1201 can be used to identify a trend in a ratio or other differential relationship of a patient Q-RV interval to the patient QRS duration. For example, a decreasing ratio can indicate a patient trend toward bundle branch block morphology (see, for example, the discussion at FIGS. 7-11 for various examples that explain how a patient Q-RV interval and QRS duration can be used to indicate a cardiac conduction dysfunction). In an example, the trendline 1201 can be monitored, and an indication or alert can be provided (e.g., using the IMD 105 or the external module 115) if the ratio is less than a threshold interval 1202 (e.g., about 0.3).

In an example, a change in the ratio or other differential relationship, such as exceeding a particular threshold rate of change (e.g., a sudden change in the ratio), can indicate a patient cardiac dysfunction. For example, a sudden change can indicate an ischemic episode, such as can be due to a bundle branch block cardiac dysfunction. In an example, such as illustrated in FIG. 12, an ischemic episode can be indicated at time 8 (e.g., corresponding to day 8, or hour 8, etc.) of Q-RV interval and QRS duration monitoring, such as where the ratio has changed by more than 0.1 relative to an adjacent data point.

In an example, one or more of an RV or LV activation duration, ratio, or other relationship (e.g., a differential relationship) between an activation duration and QRS width, can be monitored, such as over multiple cardiac cycles or other periods (e.g., periods corresponding to the periods in the chart 1200 or other periods). Such monitoring can be used to establish one or more trendlines that can indicate a patient cardiac function status. For example, when any one or more of the trendlines exceeds a particular threshold, or changes by a particular threshold rate, one or more therapies can be initiated or otherwise adjusted, or one or more alerts or indications can be provided, such as to a patient or clinician or other user, such as using the external module 115. For example, a lengthening of a patient Q-RV interval over a first duration, such as relative to a substantially stable patient QRS duration over the first duration, can indicate an ischemic episode related to a right bundle branch. In an example, a stable patient Q-RV interval over a second duration, such as relative to an increasing patient QRS duration over the second duration, can indicate an ischemic episode related to a left bundle branch. In an example, a lengthening of a patient Q-LV interval over a third duration, such as relative to a substantially stable patient QRS duration over the third duration, can indicate an ischemic episode related to a left bundle branch. In an example, a stable patient Q-LV interval over a fourth duration, such as relative to an increasing patient QRS duration over the fourth duration, can indicate an ischemic episode related to a right bundle branch.

Figure 13:
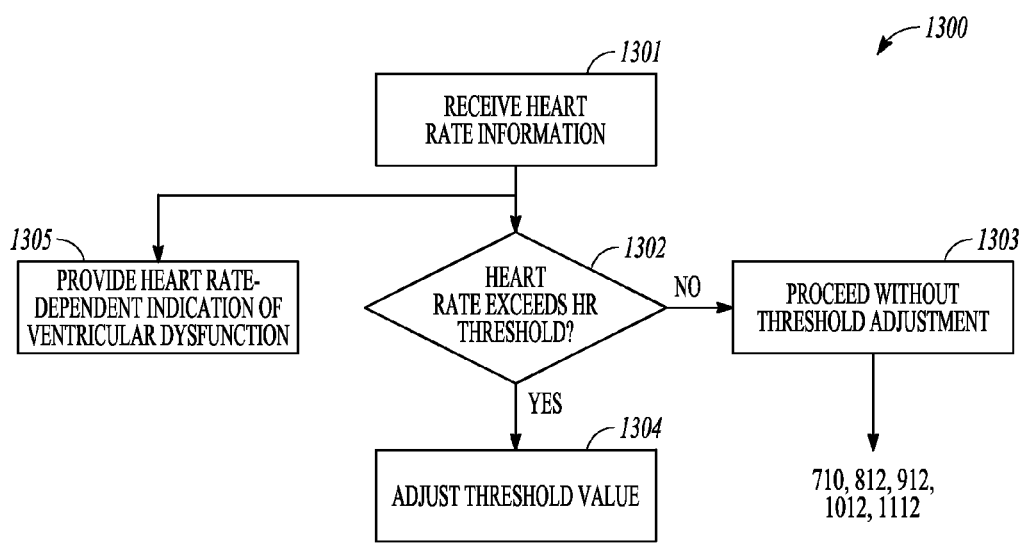
FIG. 13 illustrates generally an example that can include monitoring a patient physiological status.

FIG. 13 illustrates generally an example that can include adjusting a specified threshold value or providing an indication of ventricular dysfunction using information about a patient physiological status. One or more threshold values can be used to determine a right or left ventricular conduction dysfunction, such as according to the discussion of FIGS. 7-11. In an example, one or more of the threshold values can be adjusted, such as in response to a change in a patient physiological status.

In an example, patient physiological status can include a patient activity level, heart rate, respiration rate, minute ventilation, blood pressure, or posture, among others. Information about the patient physiological status can be received using one or more of various physiological sensors, such as can include an implantable lead, accelerometer, microphone, or impedance sensor, such as disposed on or in the IMD 105, or coupled to the implantable lead system 108, among other sensors. In an example, such as illustrated in FIG. 13, heart rate information can be received at 1301, such as using information received from one or more patient physiological sensors.

Some patients can exhibit a heart rate-dependent cardiac conduction block (e.g., a heart rate-dependent left or right bundle branch block) where a normal bundle branch cardiac signal morphology is exhibited at a baseline heart rate (e.g., in a resting state), but an abnormal bundle branch morphology is exhibited when the heart rate exceeds the baseline (e.g., when heart rate is elevated, such as due to an artificial atrial pacing therapy, or exercise, among other causes). In an example, at 1305, an indication of a heart rate-dependent cardiac conduction dysfunction can be provided. For example, at least one of a QRS duration interval, Q-RV interval, or Q-LV interval can be monitored, such as at one or more heart rates, such as according to the discussion of FIGS. 7-11. If there is a change in one or more of the QRS, Q-RV, or Q-LV intervals, such as corresponding to a change in a patient heart rate, an indication of heart rate-dependent cardiac conduction dysfunction can be provided.

In an example, the heart rate information received at 1301 can be compared to a heart rate threshold value at 1302. The heart rate threshold value can be a specified threshold value, such as a patient-specific threshold value determined using patient ECG information. In an example, the heart rate information does not exceed the heart rate threshold value and other analyses can proceed at 1303 (e.g., without adjusting a threshold value). In an example, proceeding to other analyses can include, among other scenarios, proceeding according to the discussion of FIG. 7, at 710; proceeding according to the discussion of FIG. 8, at 812; proceeding according to the discussion of FIG. 9, at 912; proceeding according to the discussion of FIG. 10, at 1012; or proceeding according to the discussion of FIG. 11, at 1112.

If the heart rate information indicates that a patient heart rate exceeds the heart rate threshold value, one or more other threshold values can be adjusted at 1304. In an example, the first threshold value, such as can be used to indicate an extended QRS width in the example of FIG. 7, at 720, can be adjusted at 1304, such as in response to information about a patient heart rate. In an example, the first threshold value can be adjusted at 1304 in response to information about one or more other patient physiological status indications, such as a patient posture indication. In an example, one or more other threshold values can be adjusted at 1304. For example, any of the first, second, third, fourth, or fifth threshold values, such as explained above in the discussion of FIGS. 7-11, can be adjusted in response to a change in a patient physiological status.

In an example, any one or more of the indications of right or left ventricular dysfunction (e.g., right or left bundle branch block, or intraventricular conduction delay) can be determined using information obtained from patients who have ICD devices that record patient cardiac signal information. For example, a paper or electronic patient report, such as including information about RV or LV activation duration, can be used to determine if a patient has a ventricular dysfunction, such as according to the analyses described above. In an example, the report can be retrieved from a comprehensive patient management system, such as to enable remote screening of ICD patients, such as to identify patients who can benefit from cardiac resynchronization therapy. In an example, the analyses described above can be implemented in the IMD 105, or the external module 115, or some other programmer, such as can be used by a clinician at patient follow-ups.

VARIOUS NOTES & EXAMPLES

Example 1 includes subject matter (such as an apparatus) comprising a processor circuit that can be configured to receive or determine a QRS duration representative of a time duration of a QRS complex, and receive or determine an RV activation duration representative of a time duration between (1) an onset of the QRS complex, and (2) an R-wave in a right ventricle. In an example, the processor circuit of Example 1 can be configured to determine whether the QRS duration exceeds a first threshold value and, when the QRS duration exceeds the first threshold value, the processor circuit of Example 1 can be configured to determine at least one of: (1) whether the RV activation duration is shorter than a second threshold value, and (2) whether a ratio or differential relationship of the RV activation duration to the QRS duration is less than a third threshold value. In an example, the processor circuit of Example 1 can be configured to provide an indication of left ventricular conduction dysfunction when it is determined that (1) the RV activation duration is shorter than second threshold value, or (2) the ratio or differential relationship of the RV activation duration to the QRS duration is less than the third threshold value.

In Example 2, the subject matter of Example 1 can optionally include a processor circuit configured to provide an indication of left ventricular conduction dysfunction to indicate Left Bundle Branch Block (LBBB), as distinguished from Right Bundle Branch Block (RBBB) or Intraventricular Conduction Delay (IVCD), when it is determined that an RV activation duration is shorter than a second threshold value, or when it is determined that a ratio of the RV activation duration to a QRS duration is less than a third threshold value. In an example, the second threshold value of Example 2 can be specified to be about 45 milliseconds, and the third threshold value of Example 2 can be specified to be about 0.3. In an example, such as in Example 2, the RV activation duration can represent a time duration between an onset of the QRS complex and an R-wave peak in a right ventricle.

In Example 3, the subject matter of one or any combination of Examples 1-2 can optionally include a processor circuit configured to determine whether a QRS duration exceeds a first threshold value and, when the QRS duration exceeds the first threshold value, determine whether an RV activation duration is shorter than a second threshold value, and provide an indication of left ventricular conduction dysfunction when it is determined that the RV activation duration is shorter than the second threshold value.

In Example 4, the subject matter of one or any combination of Examples 1-3 can optionally include a processor circuit configured to determine whether a QRS duration exceeds a first threshold value and, when the QRS duration exceeds the first threshold value, determine whether a ratio or differential relationship of an RV activation duration interval to the QRS duration is less than a third threshold value, and provide an indication of left ventricular conduction dysfunction when it is determined that the ratio or differential relationship of the RV activation duration to the QRS duration is less than the third threshold value.

In Example 5, the subject matter of one or any combination of Examples 1-4 can optionally include a processor circuit configured to determine whether a QRS duration exceeds the first threshold value and, when the QRS duration exceeds the first threshold value, determine whether a ratio of an RV activation duration to the QRS duration is less than a third threshold value, and provide an indication of left ventricular conduction dysfunction when it is determined that the ratio of the RV activation duration to the QRS duration is less than the third threshold value.

In Example 6, the subject matter of one or any combination of Examples 1-5 can optionally include a processor circuit configured to provide an indication of left ventricular conduction dysfunction to indicate Left Bundle Branch Block (LBBB), as distinguished from Right Bundle Branch Block (RBBB) or Intraventricular Conduction Delay (IVCD).

In Example 7, the subject matter of one or any combination of Examples 1-6 can optionally include a processor circuit configured to provide an indication of at least one of Right Bundle Branch Block (RBBB) or Intraventricular Conduction Delay (ICD), such as when it can be determined that (1) an RV activation duration is longer than a second threshold value; or (2) a ratio or differential relationship of the RV activation duration to a QRS duration exceeds a third threshold value.

In Example 8, the subject matter of one or any combination of Examples 1-7 can optionally include a processor circuit configured to determine a QRS duration using a signal obtained from a cardioversion or defibrillation shock electrode.

In Example 9, the subject matter of one or any combination of Examples 1-8 can optionally include a processor circuit configured to determine whether a QRS duration exceeds a first threshold value, and the first threshold value is specified between about 110 ms and about 135 ms.

In Example 10, the subject matter of one or any combination of Examples 1-9 can optionally include a processor circuit configured to determine whether an RV activation duration is shorter than a second threshold value, and the second threshold value is specified between about 40 ms and about 50 ms.

In Example 11, the subject matter of one or any combination of Examples 1-10 can optionally include a processor circuit configured to determine whether a ratio of an RV activation duration to a QRS duration is less than a third threshold value, and the third threshold value is specified between about 0.2 and about 0.4.

In Example 12, the subject matter of one or any combination of Examples 1-11 can optionally include a processor circuit configured to use trended information about at least one of an RV activation duration, a ratio or differential relationship of the RV activation duration to a QRS duration, or an indication of left ventricular conduction dysfunction, to generate an alert or to adjust a therapy control signal.

In Example 13, the subject matter of Example 12 can optionally include generating an alert that is configured to indicate at least one of myocardial ischemia or myocardial infarction, such as in response to a rate of change over a specified period of time of trended information. The trended information can include information about at least one of an RV activation duration, a ratio or differential relationship of the RV activation duration to a QRS duration, or an indication of left ventricular conduction dysfunction.

In Example 14, the subject matter of one or any combination of Examples 1-13 can optionally include a processor circuit configured to use heart rate information to adjust at least one of a first threshold value, a second threshold value, or a third threshold value, or to provide a heart rate dependent indication of left ventricular conduction dysfunction.

In Example 15, the subject matter of one or any combination of Examples 1-14 can optionally include a processor circuit configured to receive or determine an RV activation duration, wherein the RV activation duration is representative of a time duration between a heart valve closure and an R-wave peak in a right ventricle.

In Example 16, the subject matter of one or any combination of Examples 1-15 can optionally include a processor circuit configured to provide an indication of left ventricular conduction dysfunction using an activation sequence across multiple electrodes.

In Example 17, the subject matter of one or any combination of Examples 1-16 can optionally include a processor circuit configured to provide an indication of Right Bundle Branch Block (RBBB) or Intraventricular Conduction Delay (IVCD) when it is determined that an RV activation duration is longer than a second threshold value.

Example 18 includes subject matter (such as an apparatus) comprising a processor circuit configured to receive or determine a QRS duration representative of a time duration of a QRS complex, receive or determine an RV activation duration representative of a time duration between (1) an onset of the QRS complex, and (2) an R-wave in a right ventricle, and receive or determine an LV activation duration representative of a time duration between (1) an onset of the QRS complex, and (2) an R-wave in a left ventricle. The subject matter of Example 18 can optionally include a processor circuit configured to determine whether the QRS duration exceeds a first threshold value and, when the QRS duration exceeds the first threshold value, determine at least one of: (1) whether the RV activation duration is shorter than a second threshold value, (2) whether a ratio or differential relationship of the RV activation duration to the QRS duration is less than a third threshold value, (3) whether the LV activation duration is longer than a fourth threshold value, and (4) whether a ratio or differential relationship of the LV activation duration to the QRS duration is greater than a fifth threshold value. The subject matter of Example 18 can optionally include a processor circuit configured to provide an indication of left ventricular conduction dysfunction when it is determined that (1) the RV activation duration is shorter than second threshold value, (2) the LV activation duration is longer than fourth threshold value, (3) the ratio or differential relationship of the RV activation duration to the QRS duration is less than the third threshold value, or (4) the ratio or differential relationship of the LV activation duration to the QRS duration is greater than the fifth threshold value.

In Example 19, the subject matter of Example 18 can optionally include a processor circuit configured to provide an indication of Right Bundle Branch Block (RBBB) when it is determined that an LV activation duration is shorter than a fourth threshold value.

Example 20 includes subject matter (such as an apparatus) comprising a processor circuit configured to receive or determine a QRS duration representative of a time duration of a QRS complex, determine whether the QRS duration exceeds a first threshold value, receive or determine an RV activation duration representative of a time duration between (1) an onset of the QRS complex, and (2) an R-wave in a right ventricle, receive or determine an LV activation duration representative of a time duration between (1) an onset of the QRS complex, and (2) an R-wave in a left ventricle, and when the QRS duration exceeds the first threshold value, provide an indication of at least one of Left Bundle Branch Block (LBBB), Right Bundle Branch Block (RBBB), and Intraventricular Conduction Delay (IVCD), using the RV activation duration and the LV activation duration.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer- or processor-readable medium or other machine-readable medium, such as can be encoded with instructions operable to configure an electronic device to perform methods as described in the above examples. An implementation of such methods can include code, such as microcode, assembly language code, a higher-level language code, or the like. Such code can include computer-readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus comprising:
a processor circuit, configured to:
receive or determine a QRS duration representative of a time duration of a QRS complex;
receive or determine an RV activation duration representative of a time duration between (1) an onset of the QRS complex, and (2) an R-wave in a right ventricle;
determine whether the QRS duration exceeds a first threshold value and, when the QRS duration exceeds the first threshold value, determine at least one of: (1) whether the RV activation duration is shorter than a second threshold value; and (2) whether a ratio or differential relationship of the RV activation duration to the QRS duration is less than a third threshold value; and
provide an indication of left ventricular conduction dysfunction when it is determined that (1) the RV activation duration is shorter than second threshold value; or (2) the ratio or differential relationship of the RV activation duration to the QRS duration is less than the third threshold value.

2. The apparatus of claim 1, wherein the processor circuit is configured to provide the indication of left ventricular conduction dysfunction to indicate Left Bundle Branch Block (LBBB) as distinguished from Right Bundle Branch Block (RBBB) or Intraventricular Conduction Delay (IVCD) when it is determined that the RV activation duration is shorter than the second threshold value, wherein the second threshold value is specified at about 45 milliseconds, or when it is determined that the ratio of the RV activation duration to the QRS duration is less than the third threshold value, wherein the third threshold value is specified at about 0.3, and wherein the RV activation duration is representative of a time duration between an onset of the QRS complex and an R-wave peak in a right ventricle.

3. The apparatus of claim 1, wherein the processor circuit is configured to determine whether the QRS duration exceeds the first threshold value and, when the QRS duration exceeds the first threshold value, determine whether the RV activation duration is shorter than the second threshold value, and provide an indication of left ventricular conduction dysfunction when it is determined that the RV activation duration is shorter than the second threshold value.

4. The apparatus of claim 1, wherein the processor circuit is configured to determine whether the QRS duration exceeds the first threshold value and, when the QRS duration exceeds the first threshold value, determine whether a ratio or differential relationship of the RV activation duration interval to the QRS duration is less than the third threshold value, and provide an indication of left ventricular conduction dysfunction when it is determined that the ratio or differential relationship of the RV activation duration to the QRS duration is less than the third threshold value.

5. The apparatus of claim 1, wherein the processor circuit is configured to determine whether the QRS duration exceeds the first threshold value and, when the QRS duration exceeds the first threshold value, determine whether a ratio of the RV activation duration to the QRS duration is less than the third threshold value, and provide an indication of left ventricular conduction dysfunction when it is determined that the ratio of the RV activation duration to the QRS duration is less than the third threshold value.

6. The apparatus of claim 1, wherein the processor circuit is configured to provide the indication of left ventricular conduction dysfunction to indicate Left Bundle Branch Block (LBBB) as distinguished from Right Bundle Branch Block (RBBB) or Intraventricular Conduction Delay (IVCD).

7. The apparatus of claim 1, wherein the processor circuit is configured to provide an indication of Right Bundle Branch Block (RBBB) or Intraventricular Conduction Delay (ICD) when it is determined that (1) the RV activation duration is longer than the second threshold value; or (2) the ratio or differential relationship of the RV activation duration to the QRS duration exceeds the third threshold value.

8. The apparatus of claim 1, wherein the processor circuit is configured to determine the QRS duration using a signal obtained from a cardioversion or defibrillation shock electrode.

9. The apparatus of claim 1, wherein the processor circuit is configured such that the first threshold value is specified between about 110 ms and about 135 ms.

10. The apparatus of claim 1, wherein the processor circuit is configured such that the second threshold value is specified between about 40 ms and about 50 ms.

11. The apparatus of claim 1, wherein the processor circuit is configured such that the ratio or differential relationship of the RV activation duration to the QRS duration is a ratio, and wherein the third threshold value is specified between about 0.2 and about 0.4.

12. The apparatus of claim 1, wherein the processor circuit is configured to trend information about at least one of: the RV activation duration, the ratio or differential relationship of the RV activation duration to the QRS duration, or the indication of left ventricular conduction dysfunction, and to use the trended information to generate an alert or to adjust a therapy control signal.

13. The apparatus of claim 12, wherein the alert is configured to indicate at least one of myocardial ischemia or myocardial infarction in response to a rate of change over a specified period of time of the trended information.

14. The apparatus of claim 1, wherein the processor circuit is configured to receive heart rate information and to use the heart rate information to adjust at least one of the first threshold value, the second threshold value, or the third threshold value, or to provide a heart rate dependent indication of left ventricular conduction dysfunction.

15. The apparatus of claim 1, wherein the RV activation duration is representative of a time duration between a heart valve closure and an R-wave peak in a right ventricle.

16. The apparatus of claim 1, further comprising multiple electrodes, wherein the processor circuit is configured to provide the indication of left ventricular conduction dysfunction also using an activation sequence across the multiple electrodes.

17. The apparatus of claim 1, wherein the processor circuit is configured to provide an indication of Right Bundle Branch Block (RBBB) or Intraventricular Conduction Delay (IVCD) when it is determined that the RV activation duration is longer than the second threshold value.

18. An apparatus comprising:
a processor circuit, configured to:
receive or determine a QRS duration representative of a time duration of a QRS complex;
receive or determine an RV activation duration representative of a time duration between (1) an onset of the QRS complex, and (2) an R-wave in a right ventricle;
receive or determine an LV activation duration representative of a time duration between (1) an onset of the QRS complex, and (2) an R-wave in a left ventricle;
determine whether the QRS duration exceeds a first threshold value and, when the QRS duration exceeds the first threshold value, determine at least one of: (1) whether the RV activation duration is shorter than a second threshold value; (2) whether a ratio or differential relationship of the RV activation duration to the QRS duration is less than a third threshold value; (3) whether the LV activation duration is longer than a fourth threshold value; and (4) whether a ratio or differential relationship of the LV activation duration to the QRS duration is greater than a fifth threshold value; and
provide an indication of left ventricular conduction dysfunction when it is determined that (1) the RV activation duration is shorter than second threshold value; (2) the LV activation duration is longer than fourth threshold value; (3) the ratio or differential relationship of the RV activation duration to the QRS duration is less than the third threshold value; or (4) the ratio or differential relationship of the LV activation duration to the QRS duration is greater than the fifth threshold value.

19. The apparatus of claim 18, wherein the processor circuit is configured to provide an indication of Right Bundle Branch Block (RBBB) when it is determined that the LV activation duration is shorter than the fourth threshold value.

* * * * *